United States Patent [19]
Starzl et al.

[11] Patent Number: 5,542,431
[45] Date of Patent: Aug. 6, 1996

[54] HEAT DETECTION FOR ANIMALS INCLUDING COWS

[75] Inventors: Timothy W. Starzl, Boulder; Marguerita Cattell, Loveland; Richard T. Mihran; Loretta M. Zapp, both of Boulder, all of Colo.

[73] Assignee: DDX Incorporated, Boulder, Colo.

[21] Appl. No.: 176,133

[22] Filed: Dec. 30, 1993
(Under 37 CFR 1.47)

Related U.S. Application Data

[63] Continuation-in-part of Ser. No. 85,123, Jun. 30, 1993, abandoned.

[51] Int. Cl.$^6$ .................................. A61B 10/00
[52] U.S. Cl. ............................ 128/738; 119/174
[58] Field of Search .................... 128/738, 774; 119/174

[56] References Cited

U.S. PATENT DOCUMENTS

| | | | |
|---|---|---|---|
| 3,844,273 | 10/1974 | Polson | 128/2 |
| 4,247,758 | 1/1981 | Rodrian | 235/92 |
| 4,411,274 | 10/1983 | Wright | 128/738 |
| 4,503,808 | 3/1985 | McAlister | 119/1 |
| 4,618,861 | 10/1986 | Gettens et al. | 340/825.54 |
| 4,635,587 | 1/1987 | Leonardo | 119/1 |
| 4,784,155 | 11/1988 | Mills | 128/738 |
| 4,846,106 | 7/1989 | Leonardo | 119/1 |
| 4,895,165 | 1/1990 | Blair | 128/738 |
| 5,111,799 | 5/1992 | Senger et al. | 128/738 |

OTHER PUBLICATIONS

R. L. Nebel, et al., "Radiotelemetered Measures of Mounting Activity for Detection of Estrus in Lactating Dairy Cows," *Journal of Dairy Science*, Jun. 21–24, 1992, p. 291.

*Primary Examiner*—Max Hindenburg
*Attorney, Agent, or Firm*—Sheridan Ross & McIntosh

[57] ABSTRACT

A system is disclosed for making determinations related to the heat cycle in a cow. The system includes an electronic patch attached to the cow. A transmitter module for transmitting heat mount data is contained in a pouch of the electronic patch. A removable and disposable battery is also contained in the pouch for powering the transmitter module. The heat mount data from the transmitter module is sent to a repeater module to maintain the quality of the transmitted heat mount data signal. The heat mount data is re-transmitted by the repeater module to a central receiver module which includes a memory for storing heat mount data. The heat mount data is downloaded to a computer upon request using software that is also used to analyze the heat mount data. Analysis of the heat mount data results in determining a value that is useful in deciding on the optimal time to breed the cow.

56 Claims, 12 Drawing Sheets

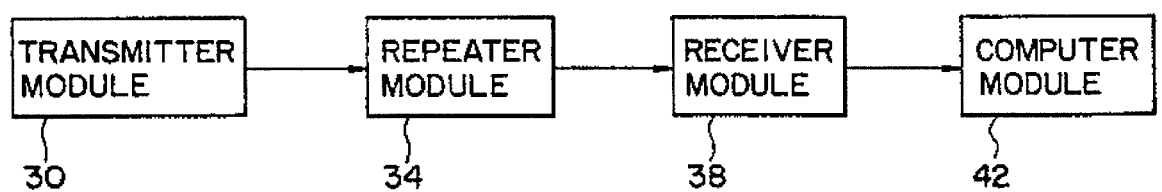
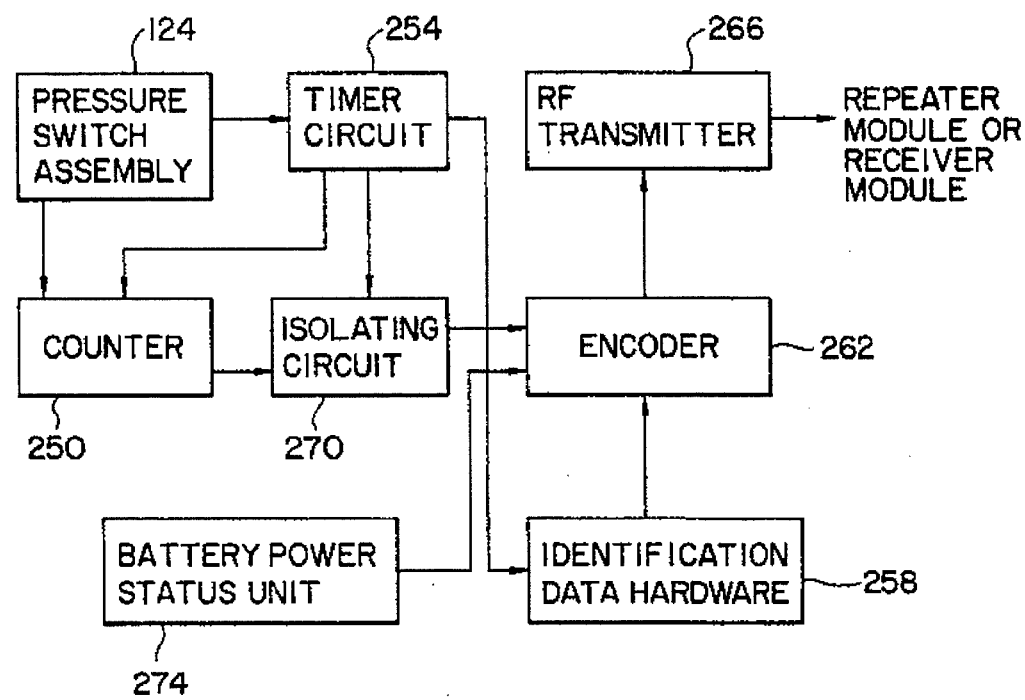

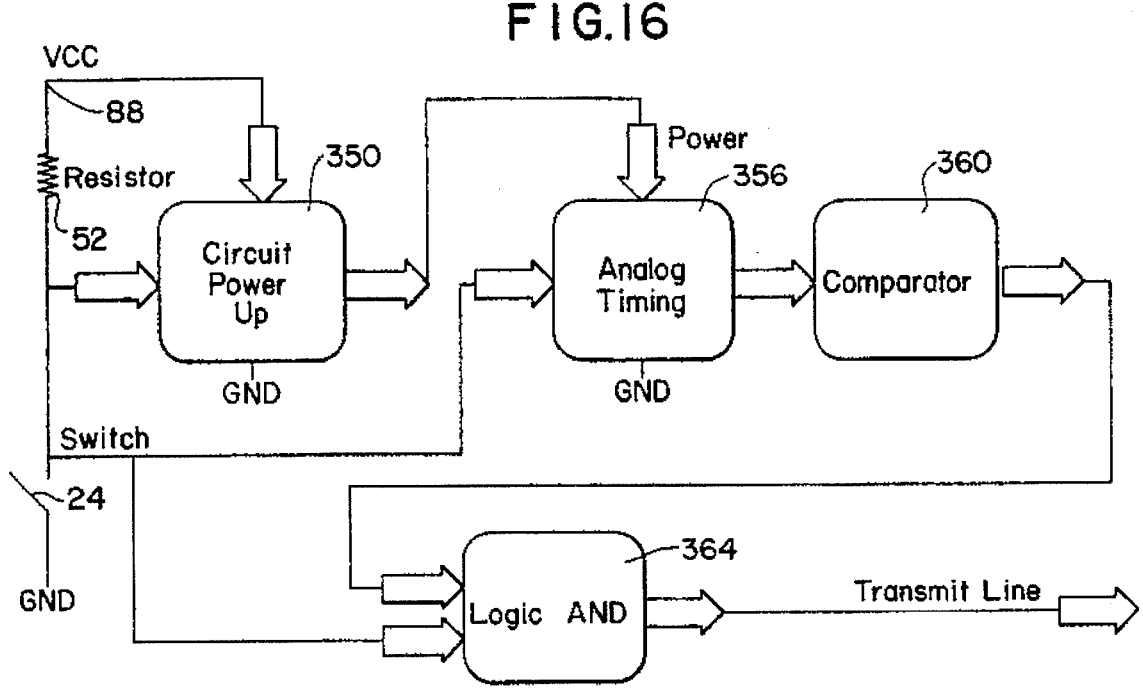

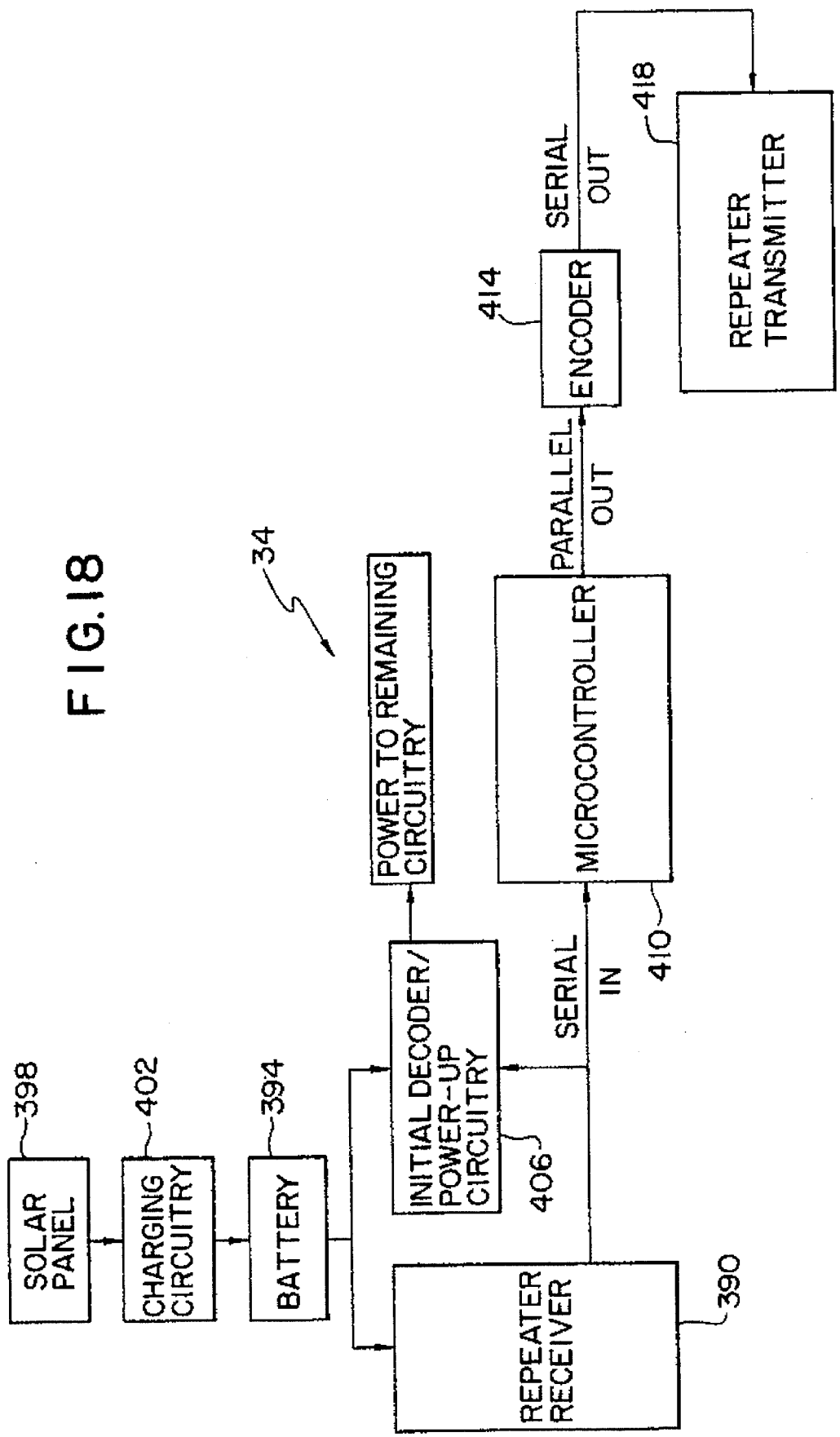

HEAT DETECTION FOR ANIMALS INCLUDING COWS

REFERENCE TO RELATED APPLICATION

This application is a continuation-in-part of U.S. patent application Ser. No. 08/085,123 filed Jun. 30, 1993, now abandoned.

FIELD OF THE INVENTION

The present invention relates to heat detection in cows and, in particular, to determining an optimal breeding time for cows.

BACKGROUND OF THE INVENTION

An accurate understanding of the estrous or heat cycle in a cow constitutes valuable information. Using this information, an accurate ovulation time period can be identified during which the cow is typically artificially inseminated. In the case of a dairy cow, a successful insemination means that desired milk production from the cow is achieved. On the other hand, a failure to achieve pregnancy in the cow usually means lost milk production for a period of time until after one or more additional heat cycles. A longer than necessary calving interval where the cow is not pregnant when she should be results in lost sales of milk.. For a herd of cows where estrus is not accurately detected, such a failure can annually cost the dairyman thousands of dollars due to milk production losses.

The importance of estrus detection in cows has been recognized in a number of issued U.S. patents. Generally, these patents describe in detail problems faced in making decisions concerning when to artificially inseminate a cow. In U.S. Pat. Nos. 4,846,106 and 4,635,587, issued Jul. 11, 1989 and Jan. 13, 1987, respectively, and entitled "Method and Apparatus for Detecting Standing Heat in Cattle," the economic significance of accurate heat detection is described. Relatedly, the relevance of cow mounts and the time periods germane to artificial insemination including the relevance of the heat cycle are also discussed. These patents disclose a module attached to the cow that displays the cow mount duration directly on the cow and also provides a warning signal to inform the cow owner that a mount has occurred.

A number of other patents disclose heat detection apparatuses. In U.S. Pat. No. 4,411,274 to Wright, issued Oct. 25, 1983 and entitled "Apparatus and Method for Monitoring the Oestrus Cycle in Female Animals" a pad is disclosed for attachment to the cow. The pad houses a transmitter module for transmitting data relating to the frequency of cow mounts. The transmitter module includes control circuitry responsive to a pressure switch that is activated when the cow is mounted. The control circuitry includes time delay circuitry for preventing signal transmission until a predetermined time lapse occurs from the time the switch is initially activated, which is independent of the length of switch activation. This transmitter module also includes an encoder and a small rf transmitter. The transmitted signal is sent to a receiving unit that includes a decoder. Printed information is provided to identify the cow that was mounted and the actual time that the mount occurred, but not the duration of the mount. U.S. Pat. No. 4,247,758 to Rodrian issued Jan. 27, 1981 and entitled "Animal Identification and Estrus Detection System" describes a transponder carried by a cow that is activatable to transmit data relating to the number of body movements of the animal and an identification number. The transponder is interrogated by a receiver before transmitting such data. U.S. Pat. No. 4,895,165 to Blair issued Jan. 23, 1990, and entitled "Electronic Estrus Detector" describes an algorithm for determining the onset of estrus that relies on the sum of all estrus mounts and the sum of all estrus mount times. This patent also indicates that the pouch attached to the cow may be made from nylon, canvas, fabric or other similar materials or combinations of such materials. U.S. Pat. No. 4,503,808 to McAlister issued Mar. 12, 1985 and entitled "Animal Herd Management System" is directed to the detection of standing heat and utilizes a transmitter implanted in the body of the animal. An identification signal uniquely identifying the animal and time of day signals are transmitted. U.S. Pat. No. 3,844,273 to Polson issued Oct. 29, 1974, and entitled "Method and Apparatus for Animal Heat Detection and Recording" relates to an electronic heat detection system that includes a transmitter unit attached to the cow and which also includes a timer that monitors the time from the beginning of a cow mount to the isolation of the cow. The transmitter unit sends transmitted data to a remote location for analysis. U.S. Pat. No. 5,111,799 to Senger et al. issued May 12, 1992 and entitled "Estrous Detection Systems" relates to a transmitting device implanted under the hide of the animal. This device includes a force responsive switch in which two contacts are forced together during a cow mount. U.S. Pat. No. 4,618,861 to Gettens et al. issued Oct. 21, 1986 and entitled "Passive Activity Monitor for Livestock" discloses a system that monitors an animal's activity by means of a transponder/activity monitor that is carried around the animal's neck and the motion thereof is used in determining the onset of estrus.

Despite the numerous proposals or disclosures directed to heat detection in cows, it appears that none of these have achieved the desired success in the market place. Consequently, a practical solution to the problem of heat detection would be significantly worthwhile to the cow owner. A practical heat detection system should be easy to implement and utilize, as well as providing for enhanced detection of estrus, while the savings realized by the herd owner is outweighed by the cost of such a system.

SUMMARY OF THE INVENTION

In accordance with the present invention, a heat detection system and methodology are disclosed for determining a value related to the occurrence of estrus in a cow for the purpose of deciding when the cow should be inseminated. In one embodiment, a combination of frequency and duration heat mount data, in which frequency refers to the number of mounts and duration refers to the time of the mount, is used. In still another embodiment, the heat cycle in the cow is determined using information additional to the frequency and duration of cow or heat mounts. This information may include intermount data, such as the temporal pattern of the heat mounts, and/or intramount data. The temporal pattern takes into account when heat mounts occurred relative to each other. Heat mounts that are grouped more densely in time are designated as having greater significance than those which occur more sporadically. This is in contrast to the frequency of heat mounts since the frequency only takes into account the number of mounts during a time period and not when they occurred during this time period. The intramount data can be characterized as either dynamic or static. With regard to dynamic intramount data or modifying parameters, such data may vary during the period of interest when a determination is made regarding a particular cow's heat cycle. Non-varying or static intramount data refers to data that does, not vary for a particular cow during the relevant time period. Variable intramount data that has been identified as being possibly useful in making determinations relevant to the cow's heat cycle includes: the ambient temperature that the particular cow is subject to and the humidity that the cow is subject to, in those cases where there is continuous monitoring of the temperature and/or humidity. With respect to substantially static data that might be useful in determining a value or values related to estrus, the following factors have been identified: the breed of the cow, the age of the cow, the time since the cow's last calving, whether the mounting cow is a frequent or infrequent mounter, whether the subject (mounted) cow frequently or infrequently mounts other cows, the surface on which the cow is supported, e.g., concrete or pasture, hilly or flat, the typical average number of mounts for the cow or other cows of the same breed and the number of cows in heat. In addition to the foregoing, in one embodiment, the present invention also takes into account relatively short duration heat mounts, while differentiating such short durations from non-mount activity such as cow "bumps and chin rests." This is accomplished by use of two different mathematical expressions or functions that express the relative significance between short and longer heat mounts.

In conjunction with obtaining the heat mount related data, an electronic patch is attached to the rear of the cow. The patch can be centered or off-set relative to the center or spine of the cow. The electronic patch includes a pouch for housing a transmitter module and a battery electrically connected to the transmitter module but located physically separate from this module. The pouch preferably has a curved shape or is flexible to conform to the cow's contours. In one embodiment, the pouch is attached to the cow via a harness. The harness is strapped to the cow so that forward-to-rearward and side-to-side motion of the pouch is limited. In this regard, the harness includes a tail tube connected by a longitudinal dorsal lattice or center straps to a neck strap and two hindquarter straps which are adjustable to securely engage the cow. In another embodiment, the pouch has a relatively rigid or semi-rigid rim and is adhesively attached to the cow. If a portion of the rim should become detached from the cow, the rigidity of the rim resists unwanted lifting or curling thereof. Consequently, the pouch better resists shear forces tending to remove the pouch from the cow. The pouch and the battery are disposable while the transmitter module is removable from the pouch for subsequent use with one or more other combinations of disposable pouches and batteries. The transmitter module is only powered on for a time sufficient to obtain cow mount data and to transmit this data, as well as other relevant data. The data transmitted includes certain identification data that is transmitted before the cow mount data. The identification data preferably includes system identification data, level identification data and transmitter or cow identification data. The system identification data is used to differentiate the transmitted data of interest from other signals that may be present from other sources. The level identification data identifies the transmission source of the cow mount data and identification data. The transmitter or cow identification data identifies the particular transmitter and, relatedly, the cow that the electronic patch is attached to. The data transmitted can also include, for example, information relating to the status of the battery power (low battery power signal), environment temperature and cow location.

In transmitting the data outputted by the transmitter module, signal transmission can be impeded by a variety of sources typically found in the cow's environment. For example, buildings or other obstacles can detrimentally impact the quality of the signal that is to be ultimately received by a receiver module. In such a case, the system employs one or more repeater modules that are advantageously located for receiving the data signals outputted by the transmitter module or a previous repeater module for ensuring that a signal of a desired strength or quality is eventually received for analysis. Each repeater module decodes and encodes received or inputted data. Preferably, a significant part of the repeater hardware is not powered on until after an initial determination is made that data of interest is being received by the repeater module.

A central receiver module communicates with the transmitter module and/or one or more repeater modules. The receiver module preferably communicates with a computer module that includes the software for analyzing the heat mount related data. The receiver module communicates with the computer module using a standard interface. The central receiver module preferably includes buffer memory for storing heat mount related data that is asynchronously received. In such a case, the computer module can include a computer, such as a PC, that is not dedicated solely to receiving and analyzing heat mount related data. When the user or owner wishes to access and analyze data, an appropriate command can be generated for downloading the heat mount data from the buffer memory to the computer module. In another embodiment, the computer module functions using an interrupt. If the computer module is inactive or in a waiting mode and an interrupt is received, available heat mount data that is present can be stored or dumped on a storage device, such as a hard disk, that is controlled by the computer module for later use, instead of using a buffer memory that may have limited storage area. The computer module can therefore be utilized for other operations including those relating to other aspects of cattle or farm management. When it is advantageous or desirable to analyze accumulated data, software for analyzing the data and making a determination as to whether the heat cycle for a cow has started, can be executed using the computer module. A computer screen displays useful information based on the analyzed data, including the identities of cows that are in their heat cycle. As previously noted, such analysis may involve the use of parameters and data obtained from sources other than the mounted cow. A peak value is used to establish the optimal breed time. This peak value corresponds to peak estrus, with peak estrus typically, centrally located at the time of peak mounting behavior. In one embodiment, the peak value is determined by first identifying the onset of estrus. The onset of estrus is detected through a sequence of mountings clustered within a certain time interval. In one embodiment, this interval is defined according to a minimum threshold, such as three heat mounts within four hours, four heat mounts within three hours, or some number of mounts and/or hours therebetween. After the onset of estrus has been identified using such a threshold, the peak estrus can been determined. The distribution of mounting behavior within estrus appears to fit a substantially symmetrical distribution, with peak estrus centrally located at the time of peak mounting behavior. Because the mounting behavior is symmetrical, the mean mounting behavior can be found at the time average of the heat mounts. For example, if there are N mounts at times $T(i)$, the peak estrus would occur at $\Sigma T(i)/N$. In a preferred embodiment, given that the longest and most significant heat mounts would occur at peak estrus, when the estrus hormones are expressed at their highest levels, this average will be weighted according to the duration and frequency of the mounts. If there are N mounts of duration D(i) occurring at times T(i), the peak estrus would occur at E[T(i)*D(i)]/ED(i)

Based on the foregoing summary, a number of salient features of the present invention are readily discerned. A practical system is provided for heat detection in cows that accurately obtains cow mount related data and may rely on other relevant factors in making a determination relating to estrus. The present system is able to be integrated with computer hardware and software that the herd owner might already have, such as a personal computer that is used in conjunction with other operations associated with cattle management. The system asynchronously gathers the heat mount data and stores the same for access upon command at any time when it is desired by the user or cow owner. It is also contemplated that other information would be gathered, such as temperature data and cow motion data. The electronic patch has disposable elements including the pouch and the battery, which are less expensive, while the transmitter module is removable and can be re-used. Under certain, commonly occurring circumstances, a repeater module is employed to ensure sufficient data signal strength and the receiver module is able to discriminate between or among the transmitter module and/or one or more repeater modules.

Additional advantages of the present invention will become readily apparent from the following discussion, particularly when taken together with the accompanying drawings.

BRIEF DESCRIPTION OF THE DRAWINGS

FIG. 1 is a block diagram of the modules or assemblies utilized in one embodiment of the present invention;

FIG. 12 is a block diagram of the transmitter module;

FIG. 16 is a block diagram of circuitry for sending heat mount data;

FIGS. 17A–17E are timing diagrams related to the operation of the circuitry of FIG. 16;

FIG. 18 is a block diagram of the repeater module;

DETAILED DESCRIPTION OF THE INVENTION

Figure 2:
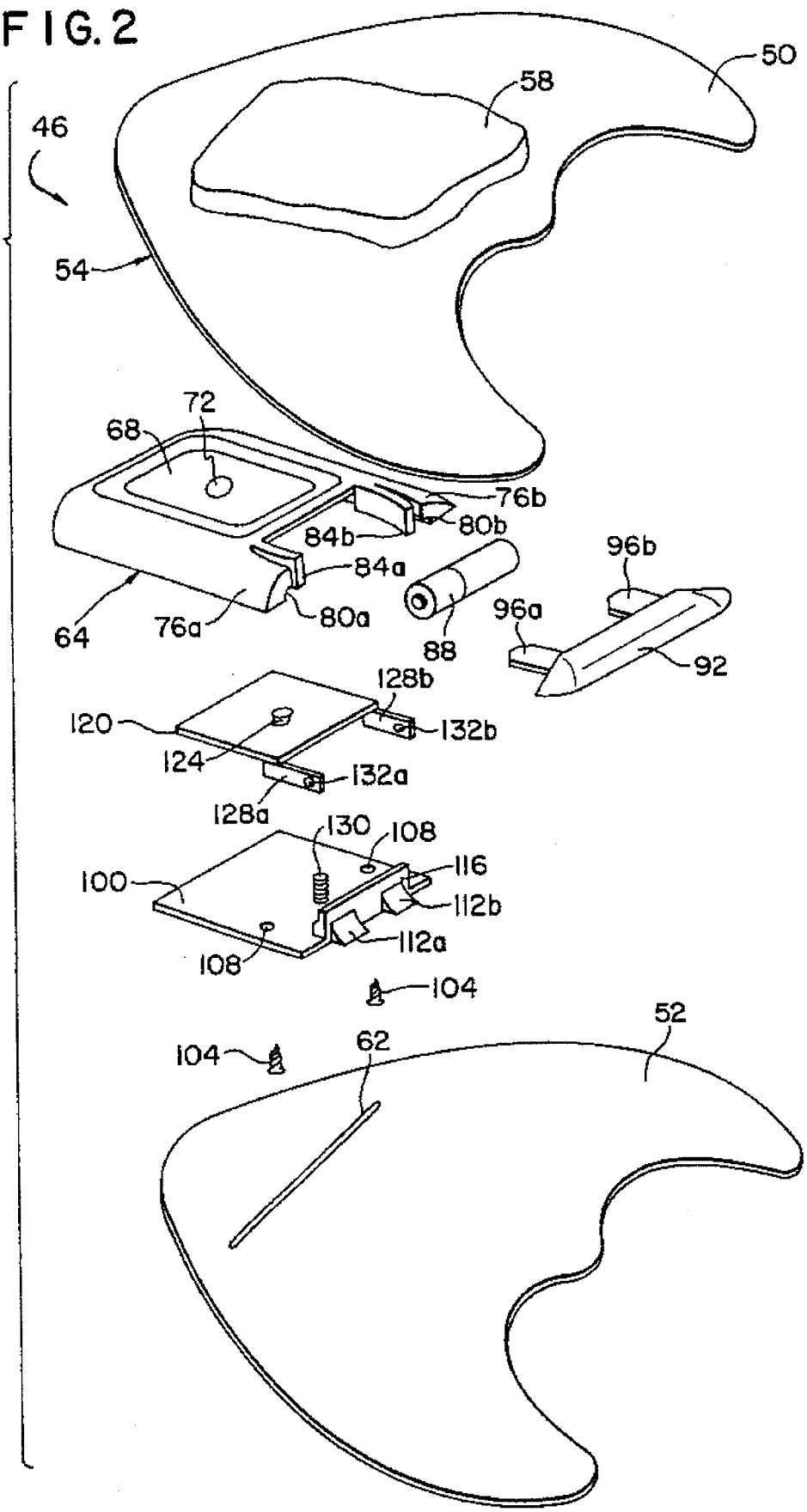
FIG. 2 is an exploded view of one embodiment of an electronic patch for attachment to a cow.

With reference to FIG. 1, a block diagram of the overall system of the present invention for detecting the heat cycle in a cow is illustrated. The system includes a transmitter module 30 for obtaining heat mount data from the cow to which it is attached. The heat mount data includes the duration of the mount. The transmitter module 30 also transmits predetermined identification data for use in discriminating data signals from other cows or other signal sources. In one embodiment, the data signals transmitted by the transmitter module 30 are received by a repeater module 34. The repeater module 34 is tuned to the frequency of the data signals outputted by the transmitter module 30 and is used to ensure the quality and strength of such data signals. In cases where there are structures or other obstacles that may interfere with the transmitted signals, a repeater module 34 is advantageously positioned to avoid the obstruction and receive the data signals from the transmitter module 30 and thereby avoid unacceptable loss or deterioration of signal strength. The data signals outputted by the repeater module 34 are then received by a central receiver module 38. The receiver module 38 is able to decode the data signals and store the heat mount and identification data in a storage memory for use by a computer module 42. It should be understood that the receiver module 38 could receive data signals directly from the transmitter module 30. That is, it may not be necessary to employ a repeater module 34 due to the lack of structures or other obstructions that could detrimentally affect the quality and strength of the data signals. In one embodiment, the receiver module 38 is able to determine whether a data signal received by it was outputted by the transmitter module 30 or a repeater module 34 using the identification data that is part of the received data signal. It should also be appreciated that it may be necessary to use more than one repeater module 34 and, in such a case, the output of a repeater module 34 is applied to next or successive repeater module(s) 34, with the last repeater module 34 acting as the source of data signals inputted to the receiver module 38. The computer module 42 includes, in one embodiment, a personal computer that is able to execute other software that the user or owner of the system might wish to utilize. When it is desirable or convenient to analyze the heat mount data and any other data used in making determinations related to the occurrence of heat in a cow, heat determining software is accessed. Concomitantly with such access, heat mount data, in one embodiment, is downloaded from the receiver module 38 to the computer module 32. The data analysis involved in determining whether estrus has occurred and the occurrence of peak estrus will be described in greater detail later. The transmitter, repeater and receiver modules will also be subsequently described with greater specificity.

Referring to FIGS. 21–24, a harness 500 for attaching the transmitter module 30 to a cow 502 is illustrated. The transmitter module 30 is securely received within a pouch 504 formed from sheets of canvas-like material. The sheets of material are stitched together at stitch lines 506 so as to define a pocket 508 for securely retaining the transmitter module 30 such that the desired positioning of the transmitter module 30 with respect to the cow 502 is maintained. An opening is provided at the front edge of pocket 508 for receiving the transmitter module 30 and allowing the transmitter module 30 to be removed for changing batteries, servicing and the like. Once the transmitter module 30 is placed inside of pocket 508, the opening 510 can be sealed using Velcro or any other suitable fastener. In this manner, the transmitter module 30 is protected against harmful elements of the outside environment.

Figure 24:
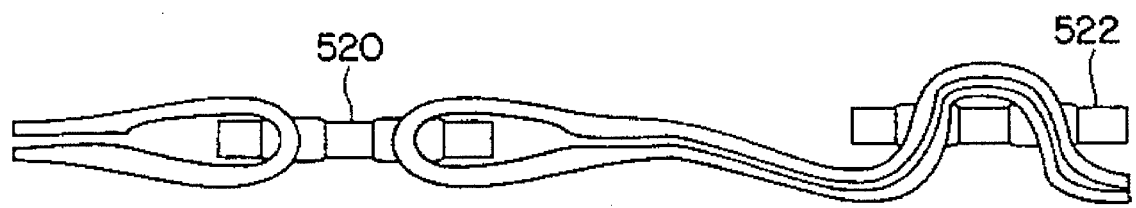
FIG. 24 is a side, cross-sectional view showing the attachment of the harness center strap and buckles of FIG. 1.

The harness 500 includes a pair of generally parallel center straps 514,516 which extend along the length of the cow's back the center straps 514,516, which are attached to the side edges of pouch 504, are separated by a distance of about 4 inches. The spacing of center straps 514, 516 is maintained by a number of cross straps 518. The center straps 514, 516 are formed from front 514a, 516a and rear 514b, 516b webs interconnected using so-called Tri-Glide buckles 520 as shown in FIG. 24. An additional pair of Tri-Glide buckles 522, in combination with buckles 520, allow for adjustment of the length of center straps 514, 516 to accommodate cows of various sizes.

For attachment to the cow 502, the harness 500 includes a tail tube 524, a pair of hindquarter straps 526, 528 and a neck strap 530. the illustrated tail tube 524, which is slipped over the cow's tail, has a circumference of about 8.75 inches and is attached to the rear edges of the center straps 514, 516. The rear edges of the hindquarter straps 526, 528 are attached to the center straps 514, 516 adjacent the rear edge of pouch 504 and the front edges of hindquarter straps 526, 528 are attached to the center straps 514, 516 at points approximately 30 inches forward of the center strap's rear edges. At each point of attachment to the center straps 514, 516, the hindquarter straps 526, 528 subtend an angle of about 60° with respect to the center straps 514, 516.

To allow for convenient attachment to the cow 502, the hindquarter straps 526, 528 are formed from front webs 526a, 528a and rear webs 526b, 528b which can be quickly interconnected and disconnected using conventional plastic snap buckles 532. The snap buckles 532 further allow for adjustment of the hindquarter strap length. Slide buckles 534 are provided on the front 526a, 528a and rear 526b, 528b webs to ease adjustment of the hindquarter straps 526, 528 and to secure straps 526, 528 once the clip attachment has been made. Similarly, the neck strap 530 is formed from left 530a and right 530b webs which are interconnected and adjusted using a conventional plastic snap buckle 536. Slide buckles 538 are provided on each of the webs 530a, 530b to ease adjustment of the neck strap 530 and to secure the strap 530 once the clip attachment has been made. The webs 530a, 530b are interconnected to the front edges of center straps 514, 516 and extend outwardly relative to center straps 514,516 such that the longitudinal axes 540, 542 of the webs 530a, 530b define an approximate 90° angle.

The dimensions of the various webs described above are selected to fit most cows allowing for adjustment. In the illustrated embodiment, each web of the neck strap 530 is about 38 inches long, the front webs 514a, 516a of the center straps 514, 516 are about 5 inches long, the rear webs 514b, 516b of the center straps 514, 516 are about 67.75 inches long, the front webs 526a, 528a of the hindquarter straps 526, 528 are about 15 inches long, and the rear webs 526b, 528b of hindquarter straps 526, 528 are about 70 inches long. The center straps 514, 516 and neck strap 530 are about 2 inches wide and the remaining straps and tail tube 524 are about 1 inch wide. All of the straps and tail tube 524 are formed from suitably durable material such as nylon or, alternatively, elastic or similar material and are interconnected via sturdy stitching. The harness 500 can be securely and conveniently attached to the cow 502 by: slipping the tail tube 524 over the cow's tail; buckling the neck strap 530 about the cow's neck and pulling the strap 530 tight using conventional plastic snap buckles 536 and buckling hindquarter straps 526, 528 about the rear legs of the cow 502 and pulling each strap 526, 528 tight using plastic snap buckles 532.

Referring to FIG. 2, one embodiment of an electronic patch 46 is illustrated. The electronic patch 46 is attached to the cow for use in obtaining heat mount data and includes the transmitter module 30 for transmitting such data. The electronic patch 46 includes an upper cover 50 and a lower cover 52 that together define a pouch or housing 54 for containing the transmitter module 30. The pouch 54 has a curved periphery and generally has a "bat" shape. This design or shape is useful in maintaining attachment to the cow. The upper cover 50 has a single layer of a desired thickness with a raised section or hollow area 58 formed in the body of the upper cover 50. The area 58 is hollow for receiving the transmitter module 30. The lower cover 52 is, in one embodiment, a multi-layer piece. A first layer, made of vinyl, is connected to the upper cover and an outer layer that is in direct contact with the cow is made of a canvas-like material. The lower cover 52 has a slit 62 located somewhat in the center portion of the body of the lower cover 52. The slit is of a size to permit insertion and removal of the transmitter module 30.

As seen in FIG. 2 wherein the transmitter module 30 is shown in connection with the generally bat-shaped pouch embodiment described above, as well as FIGS. 3 and 4, the transmitter module 30 includes a transmitter housing 64 having an upper surface 68, which has a flexible switch contact section 72. The switch contact section 72 has sufficient resiliency to allow for movement up and down when a cow mount occurs. The transmitter housing 64 includes a pair of arms 76a, 76b. Each of the arms 76a, 76b has a slot 80a, 80b, respectively, formed therein. Formed adjacent to each of these slots 80a, 80b is a wing 84a, 84b, respectively. The wings 84a, 84b are formed to have some resiliency that is useful in holding a battery 88 in a desired electrical contact position. The transmitter housing 64 also has a leg 92 with a pair of fingers 96a, 96b projecting outwardly therefrom. The leg 92 is shaped to provide the remaining side of the transmitter housing 64 and is joined thereto using the fingers 96a, 96b inserted in the slots 80a, 80b, respectively.

Figure 3:
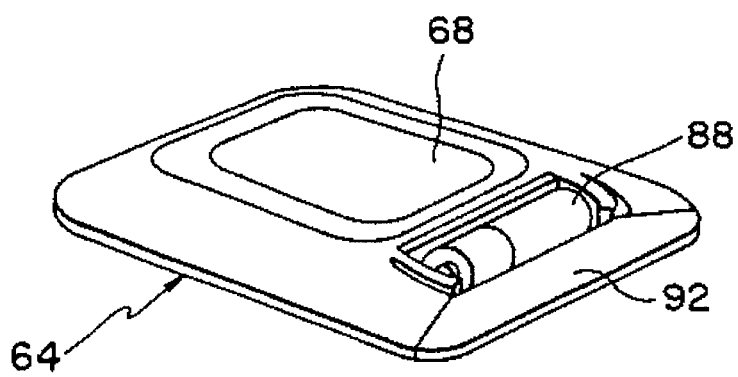
FIG. 3 illustrates a transmitter module of the electronic patch.
Figure 4:
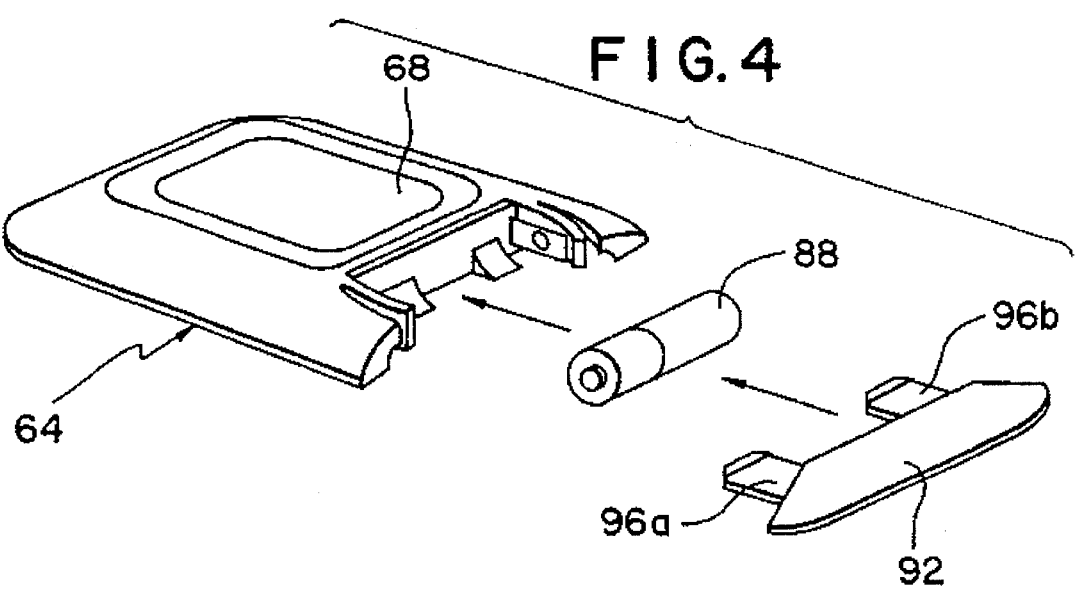
FIG. 4 illustrates removal of a battery from the transmitter module.

A base plate 100 is connectable to the transmitter housing 64 using, for example, screws 104 that are insertable through holes 108 provided in the base plate 100. In connection with holding the battery 88 in a desired position relative to the transmitter housing 64, first and second battery supports 112a, 112b are provided attached to a ledge or wall 116, which is joined to the base plate 100. Before the base plate 100 is connected to the transmitter housing 64, a transmitter printed circuit board (PCB) 120, which includes the necessary circuitry involved in transmitting useful and desired heat mount data to a remote source, is positioned in the pouch 54. This circuitry includes a pressure switch assembly 124 that is activated during a cow mount and is engaged by the switch contact section 72. First and second battery connectors 128a, 128b are attached to the transmitter PCB 120 and provide the electrical connection between the battery 88 and transmitter PCB 120 circuit paths in order to supply electrical energy to the circuitry components. As seen in FIGS. 3 and 4, after the base plate 100 is connected to the transmitter housing 64 and the base plate 100 is connected to the transmitter PCB 120 using the bolt 130, the first and second battery supports 112a, 112b are located to receive and engage the battery 88. As also seen in FIG. 4, the first and second battery connectors 128a, 128b are located adjacent to the edges of the wall 116, inwardly of the first and second wings 84a, 84b. The wings 84a, 84b are sufficiently resilient to assist in providing a solid electrical connection between the battery terminals located at the end of the battery 88 and battery contacts 132a, 132b found on each of the battery connectors 128a, 128b, respectively. Once the battery 88 is in position, the leg 92 is connected to the transmitter housing 64 using the first and second fingers 96a, 96b in order to securely hold the battery 88 in position, as seen in FIG. 3. Once the transmitter module is fully assembled including a battery 88, it can be placed into the pouch 54 through the slit 62 (or into pocket 508 of pouch 504 through opening 510). As can be appreciated, when it is necessary to replace the battery 88, the transmitter module 30 can be removed from the pouch 54 through the slit 62. The leg 92 is then disconnected from the remaining portions of the transmitter housing 64 so that the battery 88 can be removed and disposed of, while a new battery is held to the transmitter housing 64 using the leg 92. With regard to attachment of the electronic patch 46 to the cow, in one embodiment, it is positioned off-set from the spine or center of the cow. The electronic patch 46 operates appropriately at this location when the cow is mounted to provide desired heat mount data, while providing a more secure location for the electronic patch 46 and reduced wear and tear on this unit as a result of cow mountings.

Figure 5:
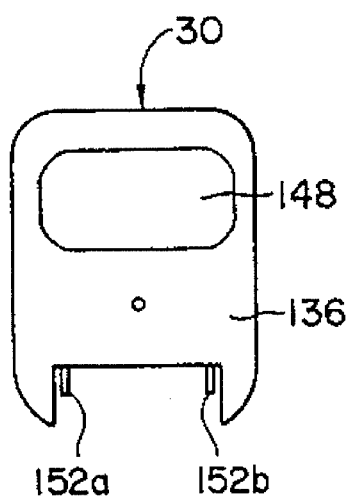
FIG. 5 is a top view of a second embodiment of a transmitter module that is characterized by the manner in which the battery is connected to the transmitter module.
Figure 6:
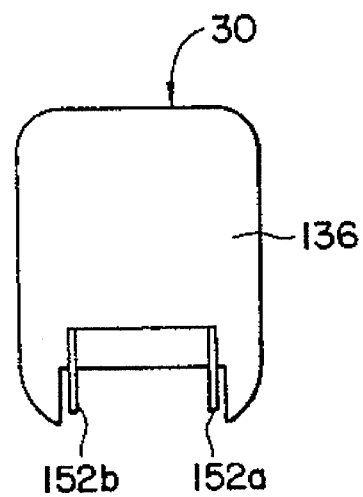
FIG. 6 is a bottom view of the transmitter module of FIG. 5.
Figure 7:
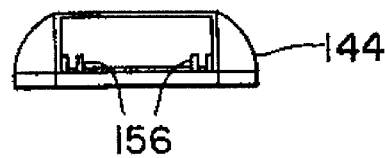
FIG. 7 is an end view of the battery housing used in the embodiment of FIG. 5.

Another embodiment for containing a removable transmitter module and a disposable battery is illustrated in FIGS. 5–7. The physical housing for the transmitter module 30 is illustrated in FIGS. 5 and 6 and includes a casing 136 that houses the transmitter PCB 120 (not shown). The casing 136 has a switch contact section 148 and a pair of transmitter terminals 152a, 152b. The transmitter module 30 is electrically coupled to a battery that is connected to a battery storage unit 144, which includes battery contact prongs 156. When completing the assembly of the electronic patch 46, in this embodiment, the transmitter module 30 is electrically connected to a battery using the two sets of battery contact prongs 156 and the transmitter terminals 152a, 152b. As can be understood, as with the other described embodiments, when the battery power becomes too low to function properly, the transmitter module 30 can be removed from the pouch 54 using the slit 62 for re-use while the battery can be disposed of, as well as the pouch 54, if necessary.

Figure 8:
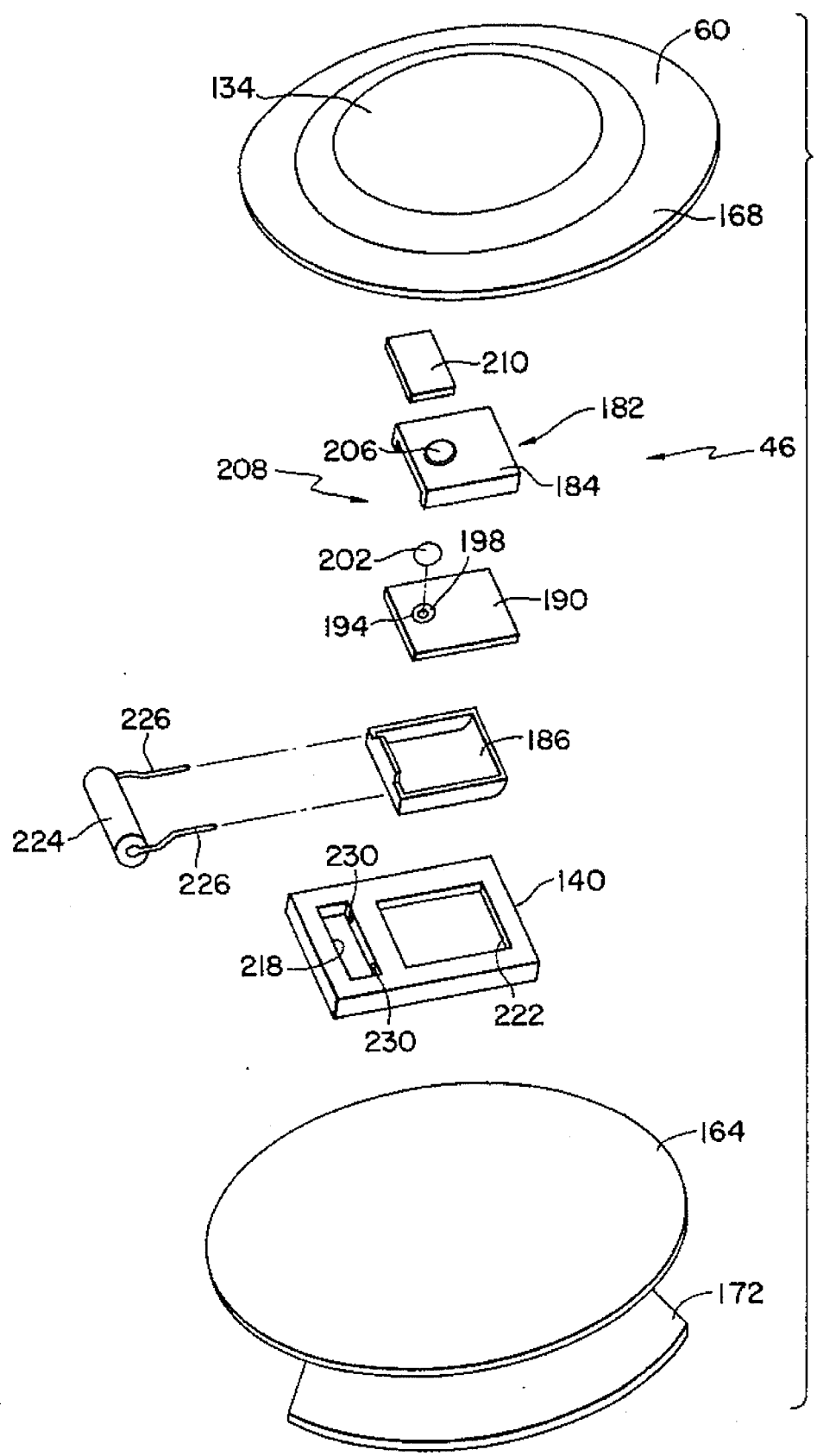
FIG. 8 is an exploded view of a third embodiment of an electronic patch.
Figure 9:
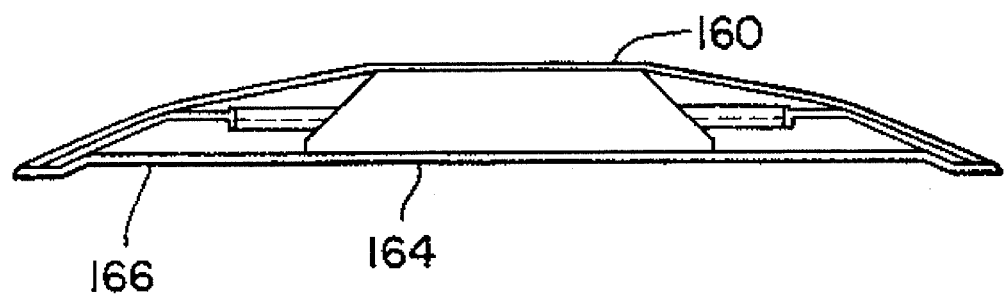
FIG. 9 illustrates a section of the pouch of FIG. 8 showing the rim thereof.
Figure 10:
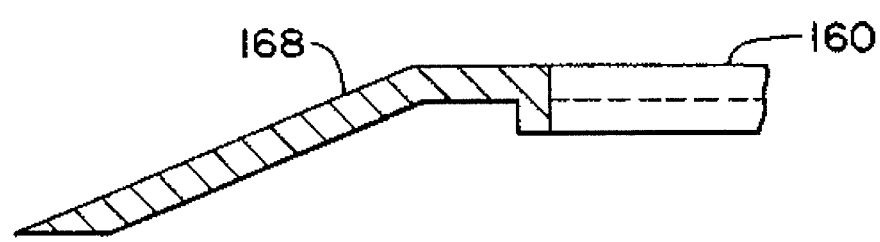
FIG. 10 is an enlarged, fragmentary section showing a straight, angled rim shape for the pouch of FIG. 9.
Figure 11:
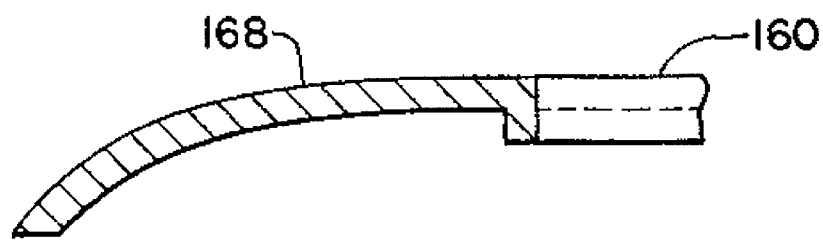
FIG. 11 is an enlarged, fragmentary section showing a curved rim for the pouch of FIG. 9.

Referring to FIGS. 8–11, a further embodiment of an electronic patch 46 is illustrated. As seen in FIG. 8, the electronic patch 46 includes an upper cover 160 and a lower cover 164 that together define a pouch or housing 166 for containing the transmitter module 30. The upper cover 160 preferably includes a rim or lip 168 that surrounds the main body portions thereof and constitutes the periphery thereof. The rim 168 is made of a semi-rigid material and which material may be more rigid than the remaining portions of the upper cover 160. The rim 168 may constitute an additional piece that is connected to the periphery of the upper cover 160. As seen in FIG. 9, the rim 168 joins the periphery of the upper cover 160 at a distance below the top of the upper cover 160. The rim 168 continues this inclination toward the lower cover 164. In one embodiment (FIG. 10), the rim 168 extends linearly outwardly. In another embodiment (FIG. 11), the rim 168 is rounded or curved. Both of these rim configurations are useful in resisting stretching of the hide, licking, shear, ripping or other mechanical forces that may be applied to the pouch while it is attached to the cow. In one embodiment, am adhesive strip 172 is attached to a section of the generally circular lower cover 164. The adhesive strip 172 is used to ensure that a moisture tight housing is achieved after the parts, including the transmitter module 30, are placed in the pouch. As seen in FIG. 8, the elements included in the pouch include a container 182 for housing the transmitter module 30. The container 182 includes a cap 184 and a base 186. Held within the container 182 is a printed circuit board 190 that forms part of the transmitter module 30 including the necessary circuitry, such as one or more integrated circuit (IC) chips. The board 190 also includes first and second annular switch contacts 194, 198, respectively. These switch contacts 194, 198 are designed to be connected or shorted together by means of a switch disk 202 that physically and electrically interconnects the two contacts 194 and 198 when a dome switch 206 is pressed or activated. The dome switch 206 is connected to the switch disk 202. These elements constitute a pressure or force switch assembly 208 for activating the transmitter module 30 for the purpose of generating heat mount data. That is, the pressure switch assembly 208 is activated by pressure thereon when a cow mounts another cow. Preferably included as part of the pressure switch assembly 208 is a linking member 210 that has a greater surface area than the dome switch 206. The linking member 210 provides more surface area for engagement by the mounting cow to facilitate activation of the pressure switch assembly 208 when a mount occurs. Also included in the pouch is the frame 140 that is generally rectangular in shape and includes an elongated cut-out section 218 and an insert area 222. The frame 140 can be made of a resilient material, such as foam. The insert area 222 is of a size to receive the transmitter module 30 that includes the pressure switch assembly 208 and the board 190, together with the housing elements 184, 186. The cut-out section 218 is of a size to contain a battery 224 that acts as the power source for the transmitter module 30. The battery 224 has terminals 226 that extend through holes 230 formed in the frame 140 adjacent to the cut-out section 218. The terminals 226 are electrically connected to power connecting ports on the board 190.

With respect to one method for making or assembling an electronic patch 46 of FIGS. 8-11, the upper cover 160 is preferably made of a vinyl or plastic that provides a relatively smooth outer surface. The lower cover 164 is preferably made of a canvas or mesh material that is porous for effectively receiving, in one embodiment, an adhesive for attachment to the cow. In the embodiment disclosed in FIG. 10, the upper and lower covers 160, 164 are of substantially the same size. In forming its desired shape, the vinyl upper cover 160 is heated and a raised section 134 is formed by means of a block being pushed through the vinyl to a desired height, with this raised height or thickness being directly related to the profile or height of the transmitter module 30 that is located in the frame 140 for location between the upper and lower covers 160, 164. The lower cover 164 is marked to indicate where the frame 140 is to be disposed thereon. An adhesive is provided outside of this marked area. The adhesive strip 172 is placed on a section of the lower cover 164 that does not have adhesive. The adhesive strip 172 preferably has a removable backing that is later removed to expose an adhesive substance. A layer of adhesive is also placed on the rim 168 of the upper cover 160 but not into the area to be occupied by the parts to be received by the pouch. With the frame 140 in the pouch and the battery 224 located in the cut-out section 218, the upper cover 160 is placed over the lower cover 164. The edges of the upper cover 160 are heated and the upper cover 160 is pressed down on the lower cover 164. In one embodiment, these steps are conducted while a vacuum is applied to the lower cover 164. The sections of the pouch not having the adhesive strip 172 heat sealed.

In this embodiment, the open section of the pouch, together with the adhesive strip 172, enable the electronic patch 46 to be finally assembled in the field. Additionally, such a structure is advantageous in utilizing disposable and reusable patch elements. Specifically, the transmitter module 30 can be provided to the user or owner outside of the pouch and inserted by the user in the field prior to use in order to complete the assembly of the electronic patch 46. The transmitter module 30 is inserted into the pouch through the open side for receipt by the insert area 212. Because the frame 140 is made of a flexible, foam material, during insertion of the transmitter module 30, the frame 140 gives or bends as the module 30 is being placed into the pouch and subsequently received by the insert area 222. After the transmitter module 30 is properly located, the tape backing of the adhesive strip 172 is removed and the pouch is tightly sealed to prevent entry of environmental elements, such as moisture, dirt or other unwanted substances into the pouch. When the battery power becomes too low for proper usage as a power source, the pouch can be opened and the transmitter module 30 removed from the frame 140. After removal, the pouch, frame 140 and the battery 224 can be disposed of while the transmitter module 30 can be re-used in another pouch that contains a frame and a new battery.

With reference to FIG. 12, the electronic components of the transmitter module 30 of one embodiment are now discussed. The pressure switch assembly 124 is activated during a heat mount. Activation of the pressure switch assembly 124 during a heat mount causes power from the battery 88 of the embodiment of FIG. 2 to be applied to the circuitry of the transmitter module 30. In a stand-by stage in which the pressure switch assembly 124 is not activated, no battery power is being applied to the transmitter module circuitry so that reduced power consumption is achieved extending the life of the battery 88. Upon switch closure of greater than a predetermined amount of time, such as 0.5 second, power is applied to a counter 250 that essentially counts pulses related to the time duration of the heat mount. That is, the counter 250 continues to count pulses beginning with the switch closure until it opens at the end of the cow mount.

At the same time that the counter 250 is counting to keep track of the heat mount duration, a timer circuit 254 is also powered on or activated. The timer circuit 254 includes power down delay circuitry that is used in maintaining necessary power to the transmitter module 30 after the pressure switch assembly 124 has been deactivated. That is, even though the switch assembly 124 is opened or deactivated because the heat mount has ended and after another delay such as 0.5 second, the heat mount data is transmitted with power being maintained for such transmission.

The timer circuit 254 also includes first and second timers for controlling the sending of the desired data. In particular, in a preferred embodiment, data sent by the transmitter module 30 comprises identification data 258 that included a system identifier, a level identifier and a transmitter module or cow identifier, as well as low battery information and error correction codes. The system identifier is used to differentiate the data of interest from other signals that may be present from other sources whereby a receiver is able to filter out or disregard signals that do not have the accompanying system identifier. The level identifier consists of information that identifies whether the transmission source is a transmitter module 30 or a particular repeater module 34. The transmission or cow identifier has information that identifies the particular transmitter module that is sending the subject data and this, in turn, identifies the cow to which this particular transmitter module is attached. Such identification data 258, in one embodiment, may be included as part of the transmitter module circuitry. After completion of the heat mount, the timer circuit 254 controls the inputting of the system identification data, level identification data and cow identification data to an encoder 262 that modulates or encodes the identification data with a carrier signal. In one embodiment, the encoder 262 is a trinary encoder in which more output combinations are achievable for the same number of input lines, in comparison with a binary arrangement. The encoded identification data is then applied to a conventional rf transmitter 266 for transmitting this data at predetermined frequency. In one embodiment, the transmitter module 30 sends the identification data as one word or block of data and this transmission is repeated seven times.

After the repetitive transmission of identification data for a predetermined amount of time, the first timer of the timer circuit 254 times out whereby the sending of identification data is stopped and a second timer of the timer circuit 254 is enabled. The second timer causes the isolating circuit 270 to output the total count of the counter 250 to the encoder 262 with the total count representing the heat mount duration for the particular, just completed, mount. The isolating circuit 270 acts as a latch to hold or store the mount data until it is to be transmitted, i.e., upon enablement of the second timer of the timer circuit 254. With this heat mount data now inputted to the encoder 262, it is also modulated or encoded and subsequently applied to the rf transmitter 266 for subsequent transmission. In one embodiment, the mount duration is also transmitted repetitively for a predetermined amount of time, e.g., about three seconds, or a predetermined number of times.

In addition to the duration time, a battery power status unit 274, in one embodiment, inputs a status bit to the encoder 262 and that state of this bit indicates whether or not the battery power is low. This information can be used to inform the user that the battery 88, and perhaps its accompanying pouch 54, should be replaced. After the second timer times out, the power down delay circuitry of the timer circuitry 254 is no longer used in supplying power and the transmitter module 30 is powered down until the pressure switch assembly 124 is once again activated.

In one embodiment, the power down delay circuitry includes a RC network that is charged during the time that battery power is applied when the pressure switch assembly 124 is activated and discharges over a predetermined time in providing the successive, repetitive transmissions of identification data and then heat mount data, together with a battery power status bit. The battery power status unit 274 monitors the power output of the battery 88 and changes its output when a predetermined minimum level of battery power is reached indicating a low power state. In one embodiment of the timer circuit 254, a clock that is used to clock out data to be transmitted from the encoder 262 is the same clock utilized by the counter 250 in monitoring the time during which the pressure switch assembly 124 is activated. In one embodiment, the counter 250 is able to keep track of up to about 32 seconds for each heat mount. In connection with the analysis involving heat mount related data, it may not be necessary to keep track of the complete mount time. That is, each mount that exceeds a predetermined time interval may be given the same significance in the analysis. If the mount continues for more than about 5–7 seconds, for example, is may not be necessary to keep track of mount time greater than this predetermined time.

The timer circuit 254 also includes circuitry that compensates for momentary deactivation of the pressure switch assembly 124 during the occurrence of a single mount. During a mount, the force applied by the mounting cow to the pressure switch assembly may momentarily be lost, for example, due to movement or shifting by the mounting cow. This temporary loss of force may cause the electrical contacts of the pressure switch assembly 124 to open, which leads to discontinuance of the counting by the counter 250 and an inaccurate indication that the mount has been completed. In one embodiment, the timer circuit 254 utilizes a threshold related to time and, unless this predetermined threshold magnitude of time is exceeded due to deactivation of the pressure switch assembly 124, the counter 250 continues to count and keeps track of time in accordance with the occurrence of a single mount. That is, instead of the momentary deactivation of the pressure switch assembly 124 causing an indication that the mount has been completed, the timer circuit 254 maintains the counting and the monitoring of mount time, unless the predetermined threshold of time was exceeded.

In a preferred embodiment, the hardware circuits and operations thereof in connection with FIG. 12 can be substantially replaced by a programmed microcontroller. The microcontroller performs the counting operation to monitor the heat mount time. The identification data is coded into the microcontroller. The microcontroller also controls the discontinuance of the transmission by keeping track of the number of times that the transmission has been repeated. After the predetermined number of times, the transmission is stopped.

The transmitter module 30 also allows the system of the present invention to keep track of apparent "cow bump" or "chin rest" information. Such information could be used to provide supervisory status and/or as a further estrus indication. In the case of a cow bump or chin rest that typically occurs for only a relatively short duration of time, the transmitter module 30 is powered on. As a result of the transmitter module 30 being activated, together with the identification data, the module 30 also transmits data corresponding to this short time duration. This data can be stored and later analyzed to determine that such data relates to non-mount activity, such as a bump or chin rest. This data is then useful in assuring that the patch 46 is still attached to the cow. For example, if anticipated cow bump information is not received for a period of time, a conclusion may be reached that the electronic patch 46 is not on the cow or the cow has not returned to heat. The monitoring of cow bumps or chin rests acts to provide asynchronous status information relating to correct system operation. By the foregoing, patch status is provided without a need for controlled generation of status information. As a consequence, power consumption is reduced over that required where periodic status information is generated and, in such a case, a less expensive battery can be employed. Additionally or alternatively, cow bumps and/or chin rests are a potential data source related to the cow's heat cycle. For example, such data can be compared with a reference or standard number of bumps and/or chin rests for a particular period. If the reference number of bumps or chin rests is exceeded, this information may be a useful indicator that the particular cow is in heat because of such increased activity.

Figure 13:
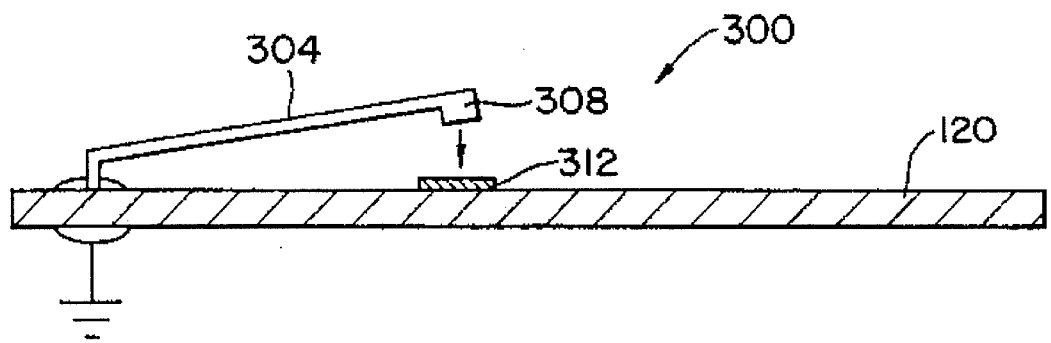
FIG. 13 is a schematic diagram illustrating one embodiment of cow motion detection device.

In another embodiment, a further switch unit is employed for monitoring cow activity. A motion or accelerometer switch unit is attached to the cow at a desired location. This switch unit is contained on the transmitter board. The accelerometer switch unit could be used to monitor cow movements related to such activities as cow walking or running, movement of cow limbs or head, and contact by the cow with objects or structures, such as fences or trees. The frequency and duration of such activity can be correlated with heat mount data, as well as cow bump and chin rest information, to further contribute to the determinations made related to the cow's heat cycle. A number of implementations can be made of such an accelerometer switch unit as depicted, for example, in FIGS. 13–15. As illustrated in FIG. 13, the accelerometer switch unit 300 includes a switch member 304 that is soldered or otherwise connected to the printed circuit board 120. The switch member 304 is a spring steel part having a weighted end 308. An electrical contact 312 is provided on the circuit board 120 in alignment with the weighted end 308. When there is sufficient, predetermined acceleration, the weighted end 308 will electrically contact the pad 312 completing an electrical circuit path. With this switch closure, a transmission can be initiated with a zero time indicated duration. The mechanical characteristics or a threshold of the switch unit 300 can be adjusted such that a predetermined number of such transmissions occur, on the average, per day. Such an average may be about 1–3 transmissions/day. As can be appreciated, a malfunctioning or lost electronic patch 46 will not generate the supervisory signals. In such a case, the system can alert the user to a possible problem with that specific electronic patch.

Figure 14:
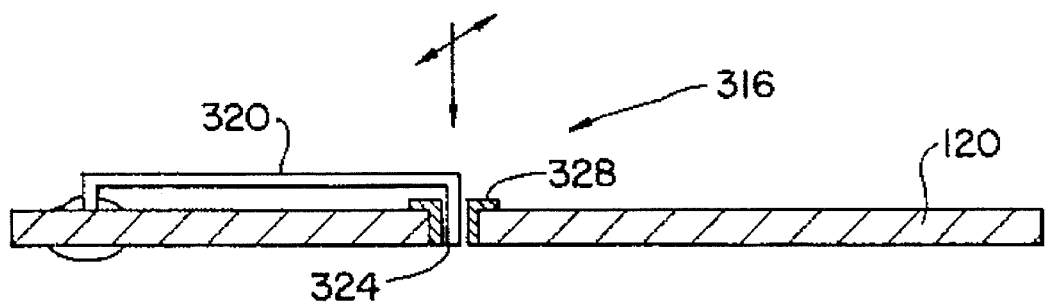
FIG. 14 is a schematic diagram of another embodiment of a cow motion detection device.

Another embodiment of an accelerometer type of switch is illustrated, in FIG. 14. This electrometer switch unit 316 also includes a switch member 320 soldered to or otherwise electrically connected to PC board 120. In this embodiment, the board 120 has an opening 324 for receiving a cylindrical electrical pad 328 having a lip. Like the embodiment of FIG. 13, the switch member 320 is a spring steel piece or wire and, in this embodiment, has its free end bent at about 90°. This free end is positioned within the bore of the pad 328, with a desired space or gap provided between the inner wall of the electrical pad 328 and the switch member free end. There is also a space between the switch member 320 and the electrical pad lip. When sufficient, predetermined accelerations occur that are either normal to or parallel with the plane of the board 120, or both, a momentary closure of the switch unit 316 occurs. As with the embodiment of FIG. 13, the transmission is initiated with a zero time indicated duration. The relative height of the switch member 320 relative to the board 120 can be modified without changing its length to provide some degree of independent variation of normal and parallel activation sensitivities.

Figure 15:
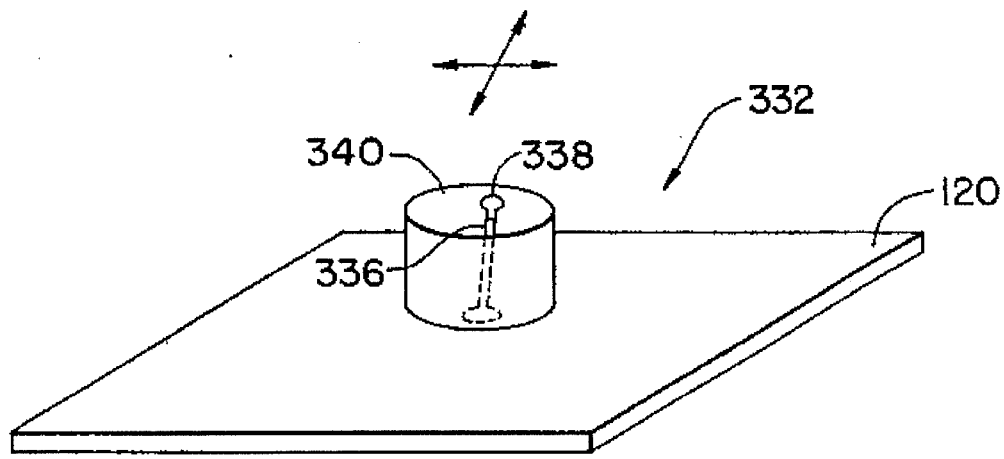
FIG. 15 is a schematic diagram of still another embodiment of a cow motion detection device.

Another implementation of an accelerometer switch is provided in the embodiment of FIG. 15. The accelerometer switch unit 332 includes a switch member 336 soldered to or otherwise connected to the PC board 120. The switch member 336 is also preferably a spring steel wire that extends essentially normal from the plane of the board 120. The switch member 336 has a contact end 338 that is used to activate the switch unit 332 when it comes in contact with an electrical contact casing 340. The conductive casing 340 has a cylindrical configuration and is attached to the circuit board 120 so that it surrounds the switch member 336 and the end of the switch member 336 soldered to the board 120 is substantially at a center position relative to the cylindrical wall of the casing 340. As with the previous embodiments, when sufficient and predetermined accelerations occur, the free contact end 338 is caused to electrically communicate with the casing 340 to generate a signal representative of a transmission having a zero time indicated duration.

With reference to FIG. 16, another embodiment for monitoring the occurrence of a heat mount is illustrated. In this embodiment, an analog technique, rather than a digital counter, is employed in providing the mount duration to be transmitted. In this embodiment, the pressure switch assembly 124 electrically communicates with a power up circuit 350 as well as being connected to the battery 88 through a resistor 352. The power up circuit 350 is always powered by the battery 88 while power to the rest of the circuitry of this embodiment is only applied when the pressure switch assembly 124 is activated. When the switch assembly 124 is activated or closed, a ground is applied to the power up circuit 350, as well as to an analog timing unit 356. This ground or "low state" results in power from the power up circuit 350 being applied for powering on the analog timing unit 356. The power applied to the analog timing unit 356, as well as other components requiring power for this embodiment, except for the power up circuit 350, will be used to power on these components so long as the switch assembly 124 is in its low state and power will continue to be applied for a predetermined amount of time after the switch assembly 124 opens or is deactivated, as indicating the termination of the heat mount. In one embodiment, power is supplied to the remaining components of this embodiment for about 1.5 times the maximum duration of a transmission after the switch assembly 124 opens. The analog timing unit 356 acts as an analog timing circuit and includes two stages. An offset stage is initiated upon switch assembly 124 closure whereby the inputted signal is ramped past a threshold level. The second stage involves the integration or a linear charging of the inputted signal upon switch assembly 124 closure. After the switch assembly 124 is deactivated or opened, the analog timing unit 356 will discharge at the same linear rate. The output of the analog timing circuit 356 is inputted to a comparator 360. One input to the comparator 360 includes a threshold or reference level. The other input is the output from the analog timing unit 356, which is compared with the inputted threshold level. Once the threshold level or voltage is exceeded by the input from the analog timing unit 356, the output of the comparator 360 will change and remain at this changed level until the output from the analog timing unit is less than the comparator threshold voltage. The output of the comparator 360 is applied to a logic And gate 364, which also receives as one of its inputs the output from the switch assembly 124. The gate 364 logically "ANDs" the input from the switch assembly 124 and the output of the comparator 360. Only when the switch assembly 124 is open or deactivated and the output of the comparator 360 exceeds the threshold level, will the transmit line be activated or in its "high state" causing a transmission to occur. As can be understood, this results in a transmission for the time period during which the output of the comparator exceeds the predetermined threshold and starting from when the switch assembly 124 is deactivated at the end of a heat mount.

With reference to the timing diagrams of FIGS. 17A–17E, a further description of the operation of FIG. 16 is now provided. When the pressure switch assembly 124 is activated, its output goes low. At substantially the same time, power from the power up circuit 350 causes the analog timing unit 356 to turn on. During the first stage of operation of the analog timing unit 356, its output immediately ramps up past the threshold level inputted to the comparator 360 and then begins to integrate the inputted signal whereby the output voltage level from the analog timing unit 356 increases at a linear rate. In one embodiment, the analog timing unit includes a RC circuit having circuit component values for providing the predetermined linear charging rate when used in conjunction with an operational amplifier. The linear signal outputted by the analog timing unit 356 continues to increase so long as the switch assembly 124 is closed. This output is applied to the comparator 360, which changes its output once the threshold level is exceeded and this input is applied to the logic And gate 364. Since the switch assembly 124 remains activated or closed, the transmit line is low and no transmission is outputted yet related to the duration of the heat mount. However, when the heat mount ends, the switch assembly 124 is deactivated or opens thereby inputting a logic high to the And gate 364 whereby transmission begins, as seen from the timing diagrams of FIGS. 17C and 17E where the peak of the signal from the analog timing unit 356 corresponds to the activated or high signal associated with the transmit line. The analog timing unit 356 is configured so that its output signal decreases at the same or some proportional linear rate that existed when the switch assembly 124 was closed and a logic low was applied to the analog timing unit 356. During the time that the output of the analog timing unit 356 remains greater than the threshold level input to the comparator 360, the transmit line remains high. In that regard, a predetermined offset time is included as part of the transmission time. That is, once there is a switch assembly 124 closure and a ramping up of the signal outputted by the analog timing unit 356 past the threshold level, the transmission signal is generated for a predetermined amount of time. In addition to this predetermined offset time, the transmission time is a function of the duration of the heat mount. Since the offset time is known, the heat mount duration can be determined using the total transmission time and subtracting the offset time therefrom. The offset time is used to assure that heat mount data is obtained, regardless of whether or not the mount was short or long, even for heat mounts less than one second. As should be understood, such an offset time feature can also be provided in the embodiment of FIG. 12.

Referring now to FIG. 18, the repeater module 34 for receiving, in one embodiment, the transmitted data signals from the transmitter module 30 is described. The repeater module 34 is illustrated as including an rf receiver that is tuned to the frequency of the carrier signal of the transmitter module 30. A repeater receiver 390 is powered by a battery 394 and must be continuously powered on to receive data signals from a transmitter module 30 that can be sent at any time. In order to insure proper battery power, a solar panel 398 could be utilized to convert solar energy to electrical power that is applied to a charging circuit 402, although DC power could be provided by other sources.

In addition to power being continuously supplied to the rf receiver 390, the battery 394 also continuously supplies power to an initial decoder circuit 406 that receives the serial data outputted by the tuned receiver 390. This decoder circuit 406 makes an initial determination as to whether the signal having the predetermined frequency constitutes appropriate data signals associated with a heat mount or, conversely, some extraneous or noise signals that have substantially the same frequency as the carrier signal associated with the heat mount data. For example, it may be that a noise signal is received that has a power spectrum substantially the same as the power spectrum expected for the heat mount data signal. The decoder circuit 406 is able to determine at a first stage whether or not such a received signal should be subsequently decoded by turning on the remaining circuitry of the repeater module 34. Communicating with the initial decoder circuitry 406 is a micro-controller 410, which is used in decoding inputted data signals and controlling their output in a predetermined, timely manner. The micro-controller 410 includes a central processing unit (CPU) and has an internal random access memory (RAM) and memory for storing its own program. The micro-controller 410, also controls and synchronizes its operation. In connection with obtaining the intelligence that is expected to be the heat mount-related data, decoding software is executed by the micro-controller 410. The decoding software is used in separating the heat mount intelligence data from the carrier signal and comparing such received data with expected data to make sure that the inputted data signal actually represents heat mount data. The micro-controller 410 also includes transmission software that is used in controlling the output of the received heat mount data to an encoder 414. The micro-controller 410 in conjunction with its transmission software controls the outputting of data to the encoder 414 or rf transmitter 418 whereby only after the transmission has been completed by the transmitter module 30 does the micro-controller 410 permit its received heat mount data to be sent to another repeater module or to the central receiver module 38. That is, in the embodiment where the data signal frequency from a repeater module 34 is the same as the frequency of the data signal outputted by the transmitter module 30, to avoid interference and insure strength and quality of signal, the micro-controller 410 does not permit simultaneous receiving and transmitting of data signals. Only after the complete transmission is received by the repeater receiver 390, including all successive and repetitive transmissions of identification data and heat mount data, does the micro-controller 410 allow subsequent transmission.

It should be noted that it is not necessary that the frequency of the outgoing signal be the same as the incoming signal. In the case of different input and output frequencies, the output signal need not be delayed until all of the input signal data has been received.

With respect to the decoding and controlling of transmission data, the micro-controller 410 includes decoding software that analyzes the data signal that the threshold decoder 406 has determined as being transmitted by the transmitter module 30 or another repeater module. The decoding software essentially compares the intelligence of the transmitted modulated signal with expected values in determining whether the incoming data signal relates to heat mount data. As previously noted, the transmitted data from the transmitter module 30 or another repeater module includes identification data that is transmitted repeatedly for a number of seconds. If such data is present, the decoding software is able to make that determination and then subsequently decode the heat mount data when it is repeatedly transmitted after the identification data. The micro-controller 410 controls the outputting of heat mount data using transmission software by not allowing re-transmission until the complete transmission is received directed to the particular heat mount data.

In controlling the sending of the heat mount data, the micro-controller 410 is able to output identification data and the data relating to the duration of the mount in parallel fashion to an encoder 414. The parallel output facilitates power savings in the operation of the micro-controller 410. That is, after all of the data for a particular transmission is arranged in parallel fashion and outputted by the micro-controller 410, it can return to its standby state without using or requiring any power while the encoder 414 is able to encode or modulate this heat mount data for subsequent transmission. In connection with the encoding, bits representing different identification data are generated by the micro-controller 410 for encoding. These bits constitute the new level identifier data and identify the repeater module 34 as being different from a transmitter module 30 or another repeater module. This identification data is sent, together with the received battery power status bit, and the heat mount duration data. The output of the encoder 414 is applied to the rf transmitter 418 in serial fashion. As noted, in one embodiment, the rf transmitter 418 is essentially the same as the rf transmitter 266 associated with the transmitter module 30 and outputs an rf signal that includes the modulated heat mount data. The signal outputted by the encoder 414 provides a modulated signal having heat mount data. Like the operation of the transmitter module 30, the identification data is transmitted repeatedly for a predetermined number of times and then the heat mount duration data, together with the battery power status bit, are repeatedly transmitted.

Figure 19:
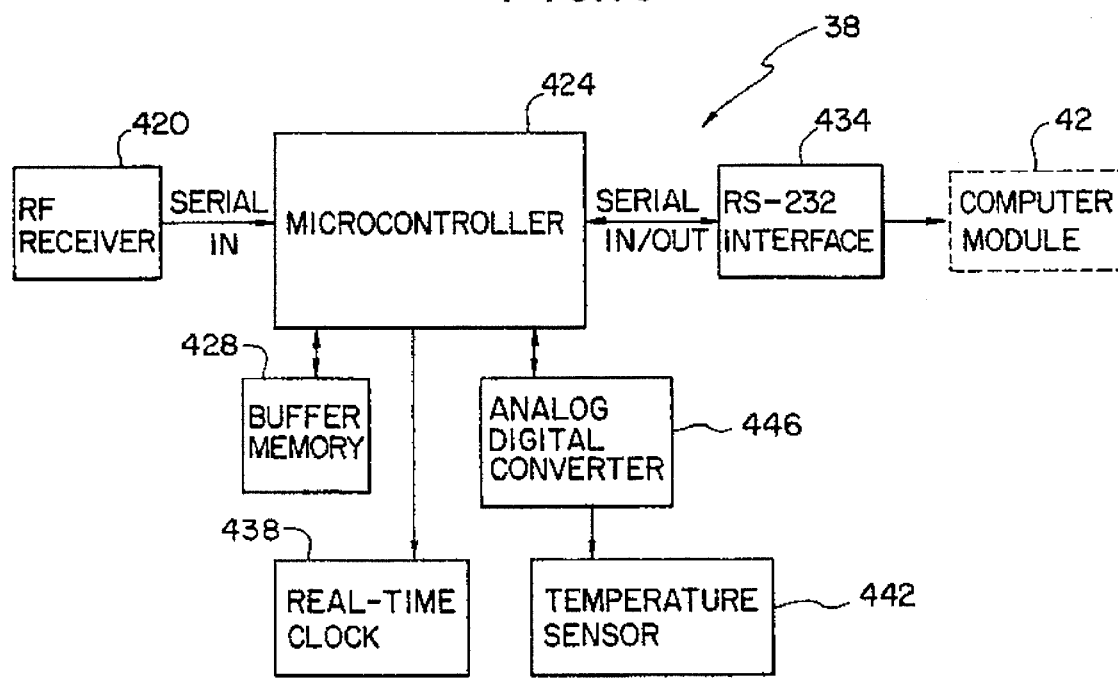
FIG. 19 is a block diagram of the receiver module.

With reference to FIG. 19, a central or base receiver module 38 is described. The receiver module 38 includes an rf receiver 420 that is tuned to the frequency associated with the modulated data signal transmitted by the repeater module 34 or a transmitter module 30. The rf receiver 420 outputs the received data signal in serial fashion to a micro-controller 424 that includes essentially the same hardware, but includes some software different from the micro-controller 410. The micro-controller 424 includes decoding software for obtaining the intelligence from the received modulated signal that represents the identification data and heat mount duration data, as well as the battery power status bit. The micro-controller 424 also includes buffering software for controlling the storage of such data in a random access memory buffer 428. The buffer memory 428 provides desired storage for heat mount data until the owner or user of the system or system software wishes to analyze it in connection with determining values related to the heat cycle for the particular or subject cow having the transmitter module 30 that transmitted such data. The buffer memory 428 allows the user to exercise ultimate control over analysis and use of the received data. Rather than requiring a dedicated computer module 42, which must always be online or ready for receipt of heat mount data, the buffer memory 428 permits a non-dedicated computer module 42 to be utilized as part of the present system. Because the computer module 42 is non-dedicated, it can be used for a number of purposes other than receiving and analyzing heat mount data. By way of example, the computer module 42 may be a conventional personal computer that is used by the owner for other farm related purposes or any desired personal purpose. When it is desirable or advantageous to analyze the recently received heat mount data at predetermined times, for example, the heat mount data stored in the buffer memory 428 can be accessed and downloaded to the computer module 42. In that regard, the micro-controller 424 also includes serial communications software involved in controlling the downloading or communication of heat mount data to the computer module 42 upon request thereof. The hardware and protocol connection between the microcontroller 424 and the computer module 42 involves the use of a standard RS-232 interface 434 that physically interconnects an available port or ports in the computer module 42 to output terminals from the micro-controller 424.

The micro-controller 424 also continuously receives an input from an internal real time clock 438. On each occurrence of the receipt of transmitted heat mount data associated with a particular transmitter module 30 for storage in the buffer memory 428, the buffering software also causes clock data to be stored with the heat mount data. The clock data thereby provides an indication as to the actual date and time of day when such heat mount data was generated. The clock data is also used as part of the analysis in determining information related to the cow's heat cycle. In one embodiment, in addition to data that is directly provided by the transmitter module 30 based on cow activities or mounts, data provided by a temperature sensor 442 is also inputted to the micro-controller 424. The temperature sensor 442 monitors the ambient temperature associated with the environment of the cows having a transmitter nodule 30. Such temperature data can also be used by algorithms of the present invention used in determining values related to the cow's heat cycle. In one embodiment, the temperature sensor 442 is a transducer that outputs an analog signal indicative of temperature to an analog-digital converter 446. The converter 446 translates the analog signal into its digital version for use by the micro-controller 424. As with the clock data, the temperature data is also stored in the buffer memory 428 using the buffering software whenever heat mount data is received so that the ambient temperature that existed for the particular cow mount is correlated therewith for potential subsequent use or analysis. In one embodiment, the temperature sensor is part of a repeater module.

In conjunction with analyzing the fundamental mount data, i.e., the duration of heat mounts during the relevant monitored period, additional data and/or other parameters, in one embodiment, can be taken into account. Such additional or secondary data can be classified into intramount and intermount data categories. Such data influences the interpretation of heat mount duration data. With respect to intermount data, it includes the temporal pattern of mounting activity. The use of the temporal pattern is based on the hypothesis that discrete heat mount data can be translated into a continuous time function which generally correlates with progesterone level in the cow. That is, each heat or cow mount is a data sample related to the changing level of progesterone in the cow. It is desirable to monitor that progesterone level and determine when that level appears to be at a maximum. Once such a determination is made, a decision can be made concerning the optimum time to breed the cow. From the temporal pattern of heat mounts, a number of values can be calculated that constitute points of a continuous function or curve over time. The peak value of this curve is then identified. This inferred function or curve is intended to correlate with the progesterone level in the cow, with the data points increasing as the progesterone level is increasing and decreasing after the peak progesterone level is reached at the peak value of the curve.

Intramount data or factors influence the relative significance that should be attributed to any given single heat mount. Such data or factors can be used to modify the duration of any single heat mount. Intramount data that has been identified includes:

(1) The ambient temperature that the cow is subject to or is experiencing. Temperature extremes influence the frequency and duration of heat mounts. A heat mount that occurs during a temperature extreme might be interpreted as having greater significance than one during a more moderate temperature.

(2) Patterns of known activity exhibited by individual cows vary widely, even under identical environmental conditions. Some cows may average only one or two mounts per heat cycle while other cows may average as many as 15 mounts. A cow exhibiting a pattern of a few mounts per heat cycle may have greater significance attached to a single mount than a cow that typically experiences a great number of mounts during a heat cycle.

(3) The number of heat cycles that have occurred since the last calving for the particular cow. Generally, heat cycles immediately after calving usually involve fewer heat mounts. Greater significance may be attached where a cow experiences a greater number of heat mounts during a heat cycle shortly after calving than normally occurs.

(4) The mounting activity of the cow could be indicative of estrus. If the subject (mounted) cow is also involved as a mounting cow, this factor also may have relative significance in indicating increased progesterone level, in comparison with the cow's normal mounting pattern.

(5) The number of other cows in heat that are part of the herd of the subject cow.

(6) The age of the cow may be taken into account. In the case in which a cow of an older calving age has the same mount activity as a cow in her prime calving age, this might be entitled to greater significance.

(7) The surface on which the cow moves or is supported may influence mount activity. The overall level of mount behavior tends to be inhibited by concrete surfaces, especially in conjunction with sub-freezing temperatures. A heat mount of a given duration at a lower temperature on concrete might be allocated relatively greater significance than similar mounts occurring on ground or pasture land at a higher temperature.

(8) Heat mount activity is known to vary by the breed of the cow. Interpretation of heat mount activity should distinguish between, for example, Holstein and Jersey breeds.

(9) The humidity of the environment that the cow is subject to might influence heat mount activity. Greater relative significance might be applied to heat mount activity at higher humidity, particularly at elevated temperatures, than such activity at a more normal humidity. In arriving at humidity data, the geographic location of the cow might be used as a general indicator of expected humidity. For example, if continuous humidity monitoring is not practical, a look-up table correlating humidity values and geographic locations (zip codes) could be utilized.

In addition to the foregoing, the significance of the particular mounting cow, not just the mounted cow, may be taken into account. For example, a subject cow mounted by a frequent/non-frequent mounting cow may be given different mounting significance, in comparison with heat mounts involving mounting cows that display a normal (standard) pattern of mounting.

Figure 20:
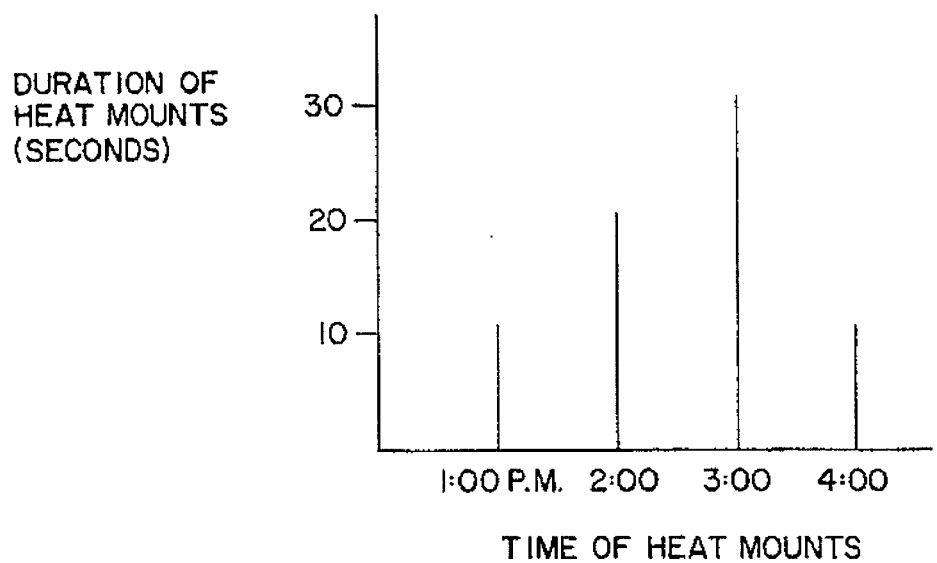
FIG. 20 is a graph illustrating heat mounts occurring at certain times for use in determining a peak estrus value.
Figure 21:
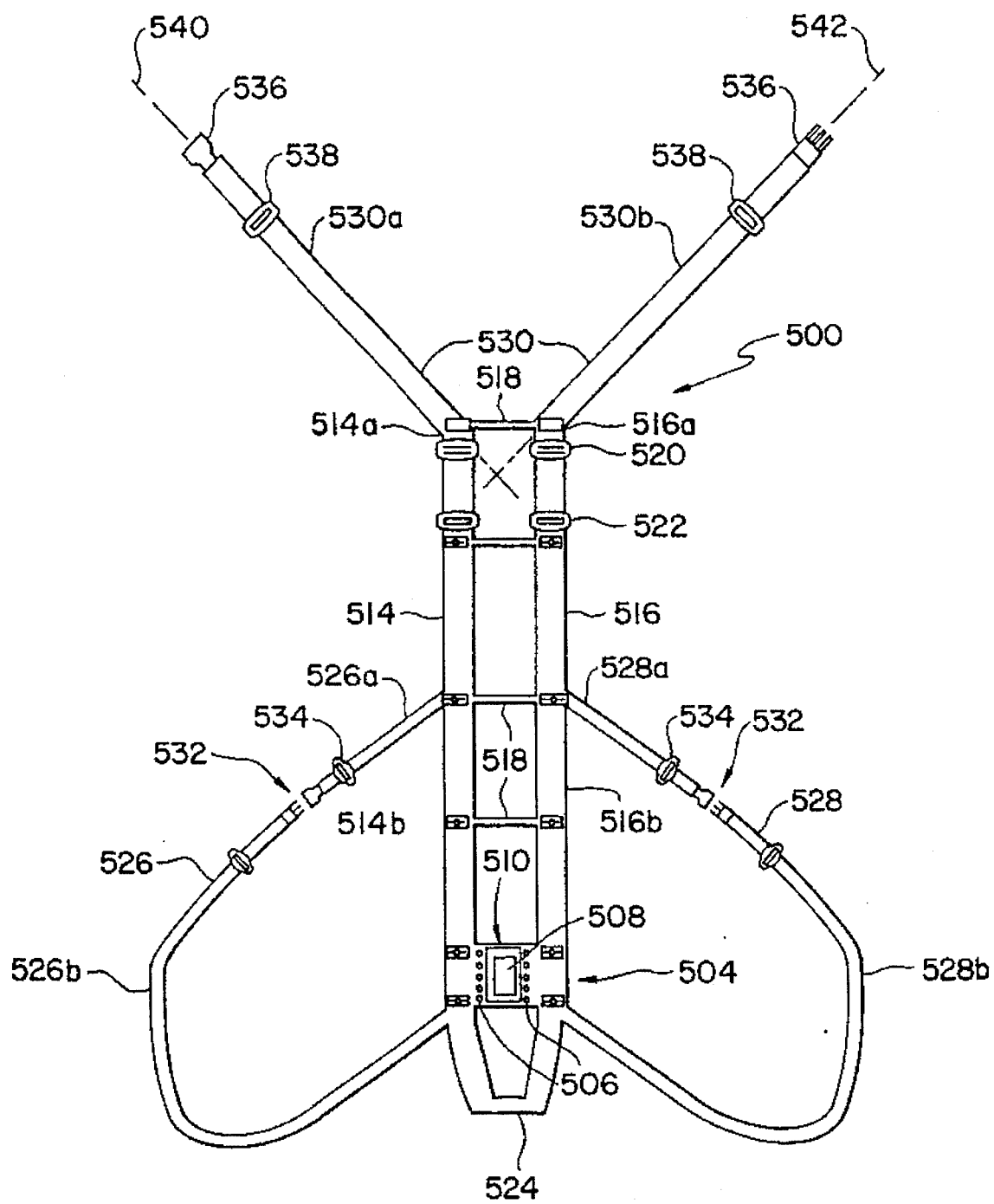
FIG. 21 is a top plan view showing a harness for attachment to a cow.
Figure 22:
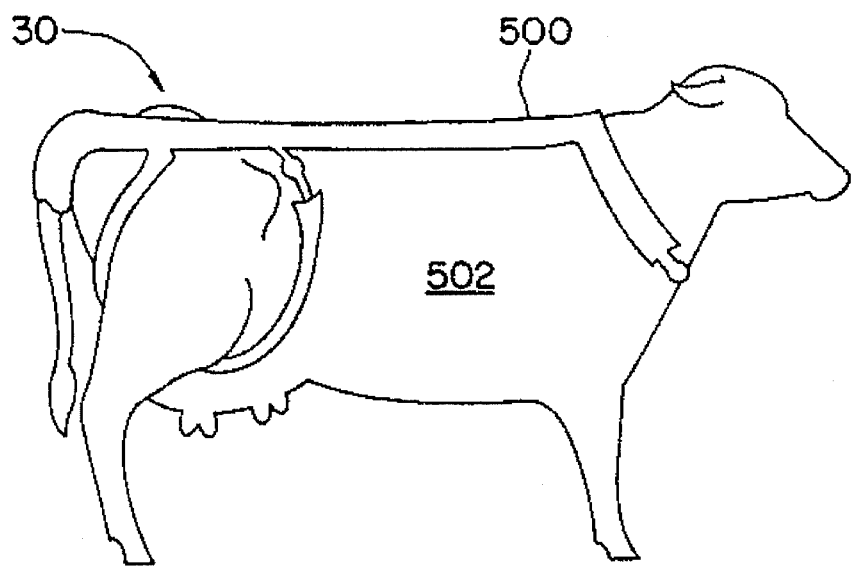
FIG. 22 shows the harness of FIG. 21 attached to a cow.
Figure 23:
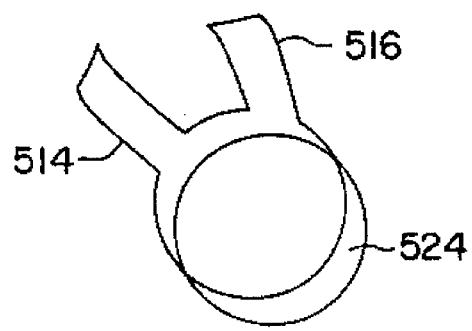
FIG. 23 is a rear perspective view showing the tail tube which is incorporated into the harness of FIG. 21.

With respect to the processing of heat mount data for making a determination regarding breeding time for a subject cow., the following description is provided, together with an explanation based on an example of heat mount data illustrated in FIG. 20. In connection with conducting the analysis in this embodiment, an onset of estrus is first detected by determining whether a predetermined threshold was met or occurred. This predetermined threshold relates to an onset of estrus based on a predetermined minimum number of heat mounts occurring within a predetermined time interval. If this predetermined threshold is met, further analysis is conducted to obtain a peak estrus value that is useful in determining an optimal, or at least desirable, breeding time. Based on investigation and studies, it has been concluded that such a predetermined threshold falls within the range of at least three heat mounts within about four hours and four heat mounts within at least about three hours. If this predetermined threshold is not met, the subsequent analysis is not performed. However, when the predetermined threshold is satisfied, further analysis is conducted to determine a peak estrus value (PEV). In that regard, it has been noted that the distribution of mounting behavior within estrus, as determined by using the predetermined threshold, appears to fit a substantially symmetrical distribution, with peak estrus centrally located at the time of peak mounting behavior. In one embodiment, because such mounting behavior is symmetrical, the mean mounting behavior is found at the time average of the heat mounts. If there are N mounts at times T(i), the peak estrus value would occur at a time: $T_{PEV}=ET(i)/N$.

In a preferred embodiment, with it being known that the longest and most significant mounts will occur at peak estrus, when the estrus hormones are expressed at their highest levels, this average can be weighted according to the duration of the mounts. If there are N mounts of durations D(i) occurring at times T(i), the peak estrus occurs at time: $T_{PEV}=E[T(i)*D(i)]/ED(i)$.

Each of these two expressions can be applied to the example of FIG. 20 that indicates a number of heat mounts occurring at certain times of determined durations. In particular, a heat mount occurs at 1 pm of duration 10 seconds, 2 pm of duration 20 seconds, 3 pm of duration 30 seconds and 4 pm of duration 10 seconds. In applying the test as to whether a predetermined threshold has been satisfied, assume that the predetermined threshold being used corresponds to at least four mounts within about three hours. Since four heat mounts occurred between 1 pm and 4 pm, the determination is made that this predetermined threshold has been met. In determining the peak estrus value, the first above-defined equation is utilized as follows:

$T_{PEV}=ET(i)/N$ $T_{PEV}=1:00+2:00+3:00+4:00/4=10/4$ $T_{PEV}=2:30$ p.m.

In employing the second of the above-defined equations, the following is determined:

$T_{PEV}=E[T(i)*D(i)]/ED(i)$ $T_{PEV}=((1\times10)+(2\times20)+(3\times30)+(4\times10))/(10+20+30+10)=180/70$ $T_{PEV}=2:34$ P.M.

As can be understood from the above calculations, each of the two expressions determines a time value at which peak estrus occurs, with the second expression weighing the time values by a corresponding duration value. The weighted time value is believed to result in a more accurate representation of peak estrus for the subject cow.

The foregoing description of the invention has been presented for purposes of illustration and description. Further, the description is not intended to limit the invention to the form disclosed herein. Consequently, variations and modifications commensurate with the above teachings in the skill or knowledge of the relevant art are within the scope of the present invention. The embodiments described hereinabove are further intended to explain the best mode or modes known of practicing the invention and to enable others skilled in the art to utilize the invention. It is intended that the appended claims be construed to include alternative embodiments to the extent permitted by the prior art.

What is claimed is:

1. An apparatus for use in making a determination related to the occurrence of estrus in a subject animal, comprising:

first means for sending heat mount data obtained as a result of a subject animal heat mount, said first means being provided with the subject animal and transmitting as a signal said heat mount data including duration data indicative of the amount of time of said heat mount of the subject animal;

second means communicating with said first means for receiving said heat mount data, said second means including a receiver to which said signal is inputted and controller means for obtaining said heat mount data from said signal, said second means also including a buffer memory for storing said heat mount data;

third means, communicating with said second means and including processing means and dedicated software, for making a determination related to the occurrence of estrus in the subject animal, wherein said third means receives said duration data including from said buffer memory and also receives time data indicating when said heat mount occurred, said processing means using said time data and said duration data indicative of the amount of time of said heat mount in determining whether a predetermined number of heat mounts occurred in a predetermined time interval, said processing means being different from said controller means and said processing means being usable for executing non-dedicated software, different from said dedicated software, when said non-dedicated software is provided with said processing means.

2. An apparatus, as claimed in claim 1, wherein:

said first: means includes a harness for attachment to the subject animal, said harness adapted for receiving a battery and a transmitter module.

3. An apparatus, as claimed in claim 2, wherein:

said harness comprises a member for engaging one of the animal's tail, the animals's neck and leg of the animal.

4. An apparatus, as claimed in claim 2, wherein:

said harness comprises straps for engaging both of the animal's rear legs.

5. An apparatus, as claimed in claim 1, wherein:

said first means includes an electronic patch attached to the subject animal, said electronic patch including a pouch having a battery and a transmitter module, said battery being electrically connected to said transmitter module wherein said transmitter module is removable from said pouch and at least one of said pouch and said battery is disposable.

6. An apparatus, as claimed in claim 1, wherein:

said first means includes a transmitter module having a switch and transmitter circuitry with said switch including an electrical contact located on a first printed circuit board and said transmitter circuitry also located on said first printed circuit board.

7. An apparatus, as claimed in claim 1, wherein:

said first means includes a transmitter module having switch means and means associated with said switch means for maintaining the monitoring of time associated with an animal mount duration, said switch means being activated when an animal mount occurs and being deactivated after the animal mount has ended, said means for maintaining including a threshold time associated with deactivation of said switch means in which a determination that said threshold time has passed is made before determining that an animal mount has ended.

8. An apparatus, as claimed in claim 1, wherein:

said first means includes a transmitter module having timer means with a power down delay circuitry for controlling removal of power to circuits of said transmitter module, said power down delay circuitry providing power to said circuits after an animal mount has ended.

9. An apparatus, as claimed in claim 1, wherein said first means includes:

counter means for counting pulses related to the duration of an animal mount;

encoder means for encoding heat mount data related to the duration of an animal mount; and isolating circuit means communicating with said counter means and said encoder means for providing a buffer between said counter means and said encoder means.

10. An apparatus, as claimed in claim 1, wherein:

said first means includes a transmitter module having fourth means for providing identification data, said identification data includes first identification data related to an identity of said transmitter module and second identification data related to an identity of a source of transmission of heat mount data.

11. An apparatus, as claimed in claim 10, wherein:

said transmitter module includes first timer means for use in controlling the sending of said identification data and second timer means for controlling the sending of heat mount data related to the duration of an animal mount.

12. An apparatus, as claimed in claim 1, wherein:

said first means includes a transmitter module having means for providing data indicative of the status of battery power used in providing power to said transmitter module and wherein said battery power status data is sent concurrently with heat mount data.

13. An apparatus, as claimed in claim 1, wherein:

said second means includes a repeater module for receiving and transmitting a data signal including heat mount data in order to maintain signal strength.

14. An apparatus, as claimed in claim 13, wherein:

said repeater module is positioned remotely from both said first means and said third means at a location that provides a substantially unimpeded path for a data signal from said first means whereby a structure in the vicinity of said first means does not cause a substantial loss of signal quality associated with said data signal outputted by said first means.

15. An apparatus, as claimed in claim 1, wherein:

said second means includes means for conserving power used by circuitry of said repeater module.

16. An apparatus, as claimed in claim 15, wherein:

said means for conserving power includes first decoding means for determining whether an inputted signal has indicia related to data generated using the apparatus.

17. An apparatus, as claimed in claim 13, wherein:

said heat mount data is controlled to be transmitted only after said repeater module has received a complete transmission of said heat mount data from said first means.

18. An apparatus, as claimed in claim 13, wherein:

said repeater module outputs a modulated data signal at substantially the same frequency as the frequency of a modulated data signal from said first means.

19. An apparatus, as claimed in claim 13, wherein:

said data signal transmitted by said repeater module includes identification data related to the identity of said repeater module distinguishing it from said first means.

20. An apparatus, as claimed in claim 1, wherein:

said second means includes a receiver module that is located more adjacent to said third means than said first means.

21. An apparatus, as claimed in claim 1, wherein:

said second means includes means for providing real time clock information for association with heat mount data.

22. An apparatus, as claimed in claim 1, wherein:

said second means includes means for receiving temperature data related to heat mount data.

23. An apparatus, as claimed in claim 1, wherein:

said controller means has buffering software for use in storing said heat mount data in said buffer memory for subsequent accessing by said third means.

24. An apparatus, as claimed in claim 23, wherein:

said controller means further includes decoding software for obtaining heat mount data from an inputted data signal and serial communication software for providing heat mount data to said third means.

25. An apparatus, as claimed in claim 1, wherein:

said processing means includes software used to download said heat mount data from said buffer memory.

26. An apparatus, as claimed in claim 1, wherein:

said duration data is used to weight a time value related to when said heat mount occurred and said third means includes means for determining a peak estrus value depending on said weighted time value and a sum value related to sail duration data for said heat mount and any other heat mount of the subject animal during a time interval.

27. An apparatus, as claimed in claim 26, wherein:

said peak estrus value equals each of said time values multiplied by a duration for said time value and with the result of each of said multiplications summed together and with the resulting sum divided by a total duration for all heat mounts occurring for said time interval.

28. An apparatus, as claimed in claim 1, wherein:

said predetermined number of heat mounts is within the range of 3–4 and said predetermined time interval is within the range of 3–4 hours.

29. An apparatus, as claimed in claim 1, wherein:

said processing means processes at least one of intermount information and intramount information, wherein said intermount information includes a temporal pattern associated with said heat mount data and said intramount information includes at least one of the following: the ambient temperature that the subject animal is experiencing, a frequency of mounting by an animal that mounts the subject animal, the breed of the subject animal, the age of the subject animal, the amount of time since the subject animal last birthed, the kind of surface that supports the subject animal, the type of confinement that the subject animal is experiencing, the humidity of the air that the subject animal is experiencing, the mounting activity of the subject animal and the geographic location of the subject animal.

30. An apparatus, as claimed in claim 1, wherein:

said first means is mounted exteriorly of the subject animal.

31. An apparatus for use in making a determination related to the occurrence of estrus in a subject animal, comprising:

first means for sending heat mount data obtained as a result of the subject animal being mounted by a mounting animal, said first means including an electronic patch having a transmitter module and a battery disposed in a pouch located exteriorly on the subject animal with said battery electrically communicating with said transmitter module, said transmitter module being removable from said pouch and said battery being removable from said transmitter module and being disposable after said removal and said transmitter module being provided with the subject animal after said battery is removed;

second means responsive to said first means for receiving said heat mount data; and third means responsive to said second means for processing said heat mount data used in making determinations related to estrus in the subject animal.

32. A method for making determinations related to the occurrence of estrus in a number of subject animals using heat mount data, comprising:

generating heat mount data when each subject animal is mounted, said heat mount data including duration data indicative of the amount of time of a heat mount, with said duration data of said heat mount exceeding a predetermined time threshold;

sending said heat mount data including said duration data over an air link;

inputting said heat mount data to processing means, said heat mount data including said duration data for each subject animal indicative of the amount of time of said heat mount, wherein time data indicative of when said heat mount occurred is provided to said processing means;

making a determination related to estrus in a first of the subject animals using said heat mount data of the first of the subject animals including said duration data indicative of the amount of time of said heat mount and said time data when said heat mount occurred; and making a determination that the onset of estrus has occurred in a second of the subject animals using secondary considerations including at least one of: (a) the second of the subject animals has no greater than two heat mounts per heat cycle with each said heat mount having duration data exceeding said predetermined time threshold and (b) historical data stored in memory related to the second of the subject animals.

33. A method, as claimed in claim 32, wherein:

said step of generating includes transmitting said heat mount data using a transmitter module, receiving said heat mount data using a repeater module and transmitting said heat mount data using said repeater module.

34. A method, as claimed in claim 33, wherein:

said transmitter module includes a switch and said step of generating includes continuing to keep track of time related to a single heat mount when said switch opens for less than a predetermined amount of time.

35. A method, as claimed in claim 32, wherein:

said step of generating includes storing said heat mount data in memory means communicating with said processing means with said heat mount data being transferred from said memory means upon a request received from said processing means.

36. A method, as claimed in claim 32, wherein:

said processing means is part of a computer for executing software other than software used in determining whether estrus has occurred in each subject animal and in which said computer initiates a downloading of said heat mount data to said computer.

37. A method, as claimed in claim 32, wherein:

said step of inputting includes inputting data other than said heat mount data obtained from each subject animal.

38. A method, as claimed in claim 37, wherein:

said step of inputting includes inputting data related to at least one of the following: the ambient temperature associated with each subject animal, the breed of each subject animal, the amount of time since each subject animal last birthed, the surface on which each subject animal is supported, the type of confinement of each subject animal, the humidity associated with each subject animal, the mounting done by each subject animal, the geographic location of each subject animal and the activity of a mounting animal that mounts each subject animal.

39. A method, as claimed in claim 32 wherein:

said making a determination related to estrus in a first of the subject animals applies greater significance to a number of heat mounts occurring over a period of time in comparison to a single heat mount that is greater in duration than each of said number of heat mounts.

40. A method, as claimed in claim 39, wherein:

said step of making a determination related to estrus in a first of the subject animals includes obtaining a first value that depends upon a temporal pattern associated with said heat mount data.

41. A method, as claimed in claim 32, wherein:

said making a determination related to estrus in a first of the subject animals includes obtaining a first value that relates to a peak estrus value with said peak estrus value related to heightened heat activity in at least one of the subject animals.

42. A method, as claimed in claim 32, wherein:

said step of inputting includes inputting variable intramount data including at least one of the following: ambient temperature associated with the second subject animal and humidity associated with the second subject animal.

43. A method, as claimed in claim 32, wherein:

said step of inputting includes inputting intramount data that is substantially static for a predetermined time interval, with said intramount data including at least one of the following: the number of heat mounts experienced by the second subject animal for a specific heat cycle; the number of heat cycles since the last birthing of the second subject animal; the age of the second subject animal; the surface on which the second subject animal is supported and the breed of the second subject animal.

44. A method, as claimed in claim 32, wherein:

said step of making a determination related to estrus in a first of the subject animals includes summing all times during which heat mounts associated with said heat mount data occurred during a time interval.

45. A method, as claimed in claim 32, wherein:

said step of making a determination related to estrus in a first of the subject animals includes obtaining a sum of the total number of heat mounts associated with said heat mount data during a time interval.

46. A method, as claimed in claim 32, wherein:

said step of making a determination related to estrus in a first of the subject animals includes summing all duration data of said heat mount data occurring during a time interval for the first subject animal.

47. A method, as claimed in claim 32, wherein:

said step of making a determination related to estrus in a first of the subject animals includes multiplying each of a number of time values related to when each said heat mount associated with said heat mount data occurred by corresponding duration data.

48. A method, as claimed in claim 32, wherein:

said step of making a determination related to estrus in a first of the subject animals includes obtaining a first value that is a peak estrus value obtained using a sum of all times when said heat mounts associated with said heat mount data of the first subject animal occurred and a sum of said heat mounts.

49. A method, as claimed in claim 32, wherein:

said step of making a determination related to estrus in a first of the subject animals includes obtaining a first value that is a peak estrus value obtained using a sum of all times when said heat mounts associated with said heat mount data of the first subject animal occurred, weighted by said duration data and a sum of said duration data for the first subject animal.

50. A method, as claimed in claim 32, wherein:

said generating step includes mounting a transmitter on the exterior of each subject animal.

51. A method for making a determination related to the occurrence of estrus in a subject animal using heat mount data, comprising:

generating heat mount data when the subject animal is mounted, said heat mount data including duration data that comprises a time interval for said heat mount of the subject animal, which time interval is determined at the subject animal using means for determining duration data attached to the animal and in which said duration data is to be used in making a determination related to estrus in the subject animal;

transmitting said determined duration data including said time interval from the subject animal to a remote station;

separately associating time data with each determined duration data, wherein each of said time data and said determined duration data is provided to processing means;

determining, after said separately associating step, whether a predetermined number of heat mounts of the subject animal has occurred in a predetermined time period using said processing means, said time data and said determined duration data; and making a determination related to the occurrence of estrus in the subject animal after said determining step.

52. A method, as claimed in claim 51, wherein:

said step of separately associating includes generating said time data at said remote station.

53. A method, as claimed in claim 51, wherein:

said step of determining includes receiving said determined duration data at said remote station using controller means and a buffer memory for storing said heat mount data.

54. A method, as claimed in claim 51, wherein:

said remote station includes dedicated software for determining whether said predetermined number of heat mounts of the subject animal has occurred in said predetermined time period and in which said processing means is usable for executing non-dedicated software, different from said dedicated software, when said non-dedicated software is provided with said processing means.

55. A method, as claimed in claim 51, wherein:

said step of determining includes, when said predetermined number of heat mounts has not occurred in said predetermined time period for the subject animal, making a determination related to estrus in the subject animal using secondary considerations including at least one of: (a) the subject animal has no greater than two heat mounts per heat cycle with each said heat mount having duration data exceeding a predetermined time threshold and (b) historical data stored in memory related to the subject animal.

56. A method, as claimed in claim 51, wherein:

said generating step includes using a transmitter located exteriorly of the subject animal.

\* \* \* \* \*